(12) United States Patent
Fadnis et al.

(10) Patent No.: US 9,512,475 B2
(45) Date of Patent: Dec. 6, 2016

(54) METHOD OF DETECTING RESIDUAL GENOMIC DNA AND A KIT THEREOF

(75) Inventors: Rahul Sharad Fadnis, Bangalore (IN); Reena Nichinmetla Raghunandan, Bangalore (IN)

(73) Assignee: Biocon Limited, Bangalore (IN)

( * ) Notice: Subject to any disclaimer, the term of this patent is extended or adjusted under 35 U.S.C. 154(b) by 78 days.

(21) Appl. No.: 14/372,690

(22) PCT Filed: Mar. 6, 2012

(86) PCT No.: PCT/IB2012/051046
§ 371 (c)(1),
(2), (4) Date: Jul. 16, 2014

(87) PCT Pub. No.: WO2013/108083
PCT Pub. Date: Jul. 25, 2013

(65) Prior Publication Data
US 2015/0031029 A1    Jan. 29, 2015

(30) Foreign Application Priority Data
Jan. 16, 2012  (IN) .............................. 164/CHE/2012

(51) Int. Cl.
*C12Q 1/68*  (2006.01)
*C07H 21/02*  (2006.01)

(52) U.S. Cl.
CPC ............. *C12Q 1/686* (2013.01); *C12Q 1/6888* (2013.01); *C12Q 2600/166* (2013.01)

(58) Field of Classification Search
CPC ................ C12Q 1/686; C12Q 1/6888; C12Q 2600/166
See application file for complete search history.

(56) References Cited

U.S. PATENT DOCUMENTS

| | | |
|---|---|---|
| 5,393,657 A | 2/1995 | Letwin et al. |
| 2009/0325175 A1 | 12/2009 | Anderson et al. |

FOREIGN PATENT DOCUMENTS

WO    WO-2013108083 A1    7/2013

OTHER PUBLICATIONS

GenBank Accession No. J00056 (Apr. 1993).*
Johansson, M.K., Meth. Mol. Biol., vol. 335, pp. 17-29 (2007).*
Applied Biosystems "Reagents and Consumables. Sequence Detection Systems", pp. 1-12 (2000).*
Weiner, M.P. et al., Biotechniques, vol. 44, pp. 701-704 (2008).*
Buck, G.A. et al., Biotechniques, vol. 27, pp. 528-536 (1999).*
International Application Serial No. PCT/IB2012/051046, International Preliminary Report on Patentability mailed Dec. 20, 2013, 18 pgs.
International Application Serial No. PCT/IB2012/051046, International Search Report mailed Jul. 9, 2012, 5 pgs.
International Application Serial No. PCT/IB2012/051046, Response filed Nov. 7, 2013 to International Search Report and Written Opinion mailed Jul. 9, 2012, 13 pgs.
International Application Serial No. PCT/IB2012/051046, Written Opinion mailed Jul. 9, 2012, 5 pgs.
Goldman, Mark, et al., "Use of Polymerase Chain Reaction for Detecting DNA Contaminants in Pharmaceutical Recombinant", Clinical Chemistry, 37(9), (1991), 1523-1525.
Nissom, Peter M, "Specific detection of residual CHO host cell DNA by real-time PCR", Science Direct, Biologicals 35, (2007), 211-215.
Venable, Daryl, et al., "High-Throughput and Quantitative Detection of Residual NS0 and CHO Host Cell Genomic DNA", BioProcess International, (Jun. 2007), 56-60, 62.

* cited by examiner

*Primary Examiner* — Teresa Strzelecka
(74) *Attorney, Agent, or Firm* — Schwegman Lundberg & Woessner, P.A.

(57) ABSTRACT

The present disclosure relates to a highly specific and sensitive method of detecting host cell impurities in a biological sample by using quantitative real time polymerase chain reaction (q PCR). The present disclosure also provides novel designed primer and probe to amplify only the specific Alu family of dispersed repetitive sequences from Chinese hamster ovary cells used for expression of therapeutic proteins.

10 Claims, 20 Drawing Sheets

Fig 1

Figure 2B:
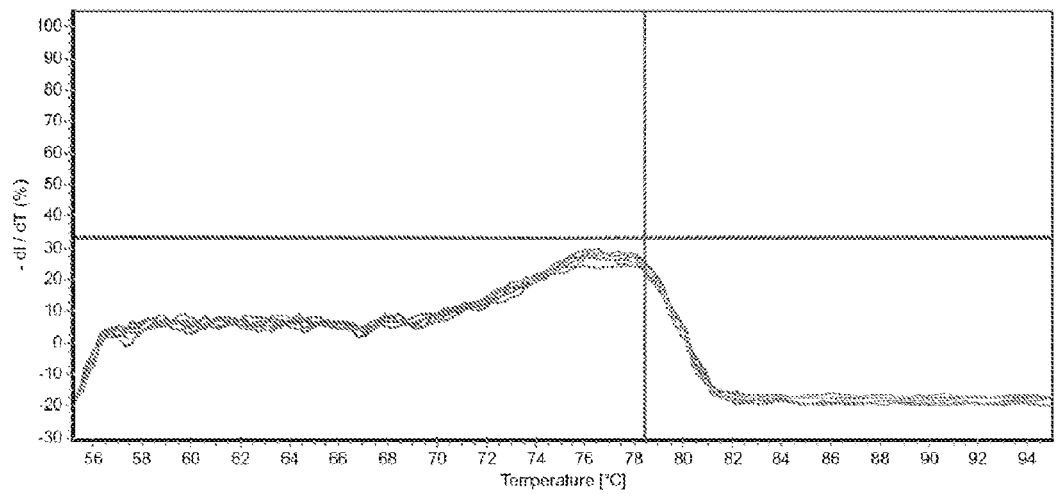

```
BioAlj       GCTGGAGAGATGGCTCGAGGTTAAGAGCACTGACTGCTCTTCCAGAGGTCCTGAGTTCAATT 62  (Seq ID
no 1)
2EG          GCTGGAGAGATGGCTCGAGGTTAAGAGCACTGACTGCTCTTCCAGAAGTCCTGAGTTCAATT 62  (Seq ID
no 2)
U315         GCTCCAGAGATGGCTCGAGCTTAACAGCACTCACTGCTCTTGACAAGTCCTCAGTTCAATT 62  (Seq ID
no 3)
289Pg        GCTGGAGAGATGGCTCGAAGTTAAGAGCACTGCTGCTCTTCCAGAGGTCCTGAGTTCAATT 62  (Seq ID
no 4)
U36          GCTGGAGAGATGGCTCGAGCTTAAGAGCACTCACTGCTCTTCCAGAGGTCCTCAGTTCAATT 62  (Seq ID
no 5)
U88          GCTGGAGAGATGGCTCGAGGTTGAGAACACTGCTGCTCTTCCAGAGGTCCTGAGTTCAATT 62  (Seq ID
no 6)
             *****************  ***  *** * ***********  **************

BioAlj       CCCAGCAACCAC 74  (Seq ID no 1)
2EG          CCCAGCAACCAC 74  (Seq ID no 2)
U315         CCCAGCAACCAC 74  (Seq ID no 3)
289Pg        CCCAGCAACCAC 74  (Seq ID no 4)
U36          CCCAGCAACCAC 74  (Seq ID no 5)
U88          CCCAGCAACCAC 74  (Seq ID no 6)
             ************
```

Fig 2a

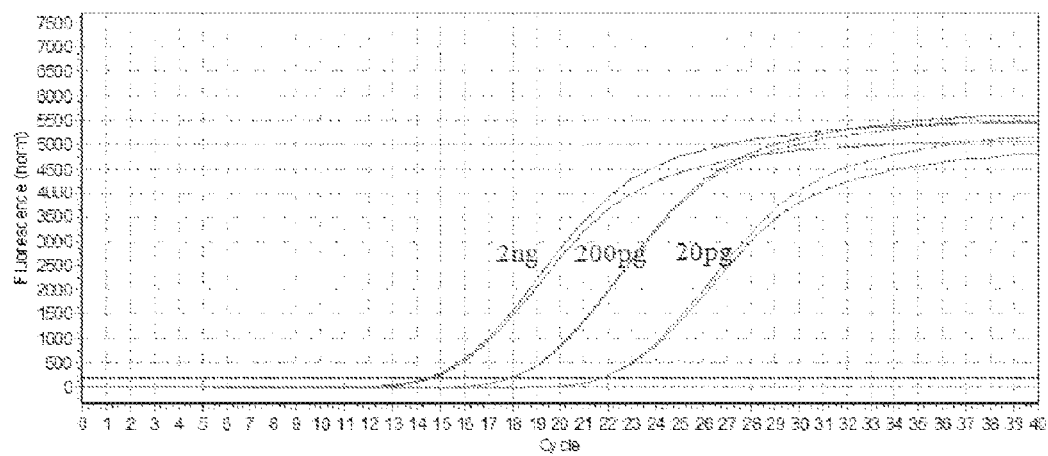

Threshold: 185 (Adjusted manually)
Baseline settings: automatic, Drift correction OFF Threshold: 33%

Threshold: 33%

TGGAGAGATGGCTCGAGGTTAAGAGCACTGGCTGCTCTTCCAGAGGTCCTGAGTTCAATTCCCAG
CAACCA

SEQ ID NO 9:

TG[GAGAGATGGCTCGAGGTTAAG]AGCACTGGCTGCTCTTCCAGAGGTCCTGAGTTCAATTCCCAGCAACCA

Complementary strand of SEQ ID NO:9 (SEQ ID NO:3'):

ACCTCTCTACCGAGCTCCAATTCTCGTGACCGACGAGAAGGTCTCCAGGACTC[AAGTTAAGGGTCGTTGGT]

SEQ ID NO:9:

TGGAGAGATGGCTCGAGGTTAAGAGCACTGGCTGCTCTTCCAGAGGTCCTGAGTTCAATTCCCAGCAACCA

Complementary strand of SEQ ID NO:9 (SEQ ID NO:31):

ACCTCTCTACCGAGCTCCAATTCTCGTGACCGACGAGAAGGTCTCCAGGACTCAAGTTAAGGGTCGTTGGT

Threshold: 42 (Adjusted manually)
Baseline settings: automatic, Drift correction OFF

Fig 9

CLUSTAL W (1.83) multiple sequence alignment-Lineage 1

```
21   ------------------------------------TGGAGAGATGGCTCGAGG  18
50   ------------------------------------TGGAGAGATGGCTCGAGG  18
7R   ---------------------------------CGATATGGAGAGATGGCTCGAGG  23
11   TTGCATGCAGGCCTCTGCAGTCGACGGGCCCGGGATCCGATTTGGAGAGATGGCTCGAGG  60
27R  TTGCATGCAGGCCTCTGCAGTCCACGGGCCCCGGGATCCGATTTGGACACATGCCTCCACG  60
13   TTGCATGCAGGCCTCTGCAGTCGACGGGCCCGGGATCCGATTTGGAGAGATGGCTCGAGG  60
                                      ****************

21   TTAAGAGCACTGGCTGTTCTTCCAGAGGTCCTGAGTTCAATTCTCAGCAACCACATGATG  78
50   T-AAGAGCACTGGCTGTTCTTC-AGAGGTCCTGAGTTCA-TTCTCAGCAACCACATGATG  75
7R   TTAAGAGCACTGGCTGTTCTTCCAGAGGTCCTGAGTTCAATTCTCAGCAACCACATGATG  83
11   T-TAGAGCACTGGCTGTTCTTCCAGAGGTCCTGAGTTCAATTCTCAGCAACCACATGATG  119
27R  TTA-GAGCACTGGCTGCTCTTCCAGAGGTCTTGAATTCAATTTCCAGCAACAACATGGTG  119
13   TTAAGAGCACTGGCTGCTCTTCCAGAGGTCTTGAATTCAATTTCCAGCAACAACATGGTG  120
      *  ***********  ****  *******  ***  ****  **  *******  *****  **

21   ACTCAAAATCATCTATAATGAGATCTGGTGCCCCCTTTTGGTGGGAAGGCATACATGCAA  138
50   ACTCAAAATCATCTATAATGAGATCTGGTGCCCCCTTTTGGTGGGAAGGCATACATGCAA  135
7R   ACTCAAAATCATCTATAATGAGATCTGGTGCCCCCTTTTGGTGGGAAGGCATACATGCAA  143
11   ACTCAAAATCATCTATAATGAGATCTGGTGCCCCCTTTTGGTGGGAAGGCATACATGCAA  179
27R  GCTCACAACCATACATGATGAGATCTGGTGCCCTCTCCTGGCCTGCAGGGATACATGCAG  179
13   GCTCACAACCATACATGATGAGATCTGGTGCCCTCTCC[TGGCCTGCAGGGATACATGCAG]  180
      ****  **  ***  *****************  **  **    *  ***  *********

21   GC-GAAGACTACATAATCAATCTTTTTTTTTTTTTTT-GGCCTGTGGGGACATTTTGTT  196
50   GC-GAAGACTACATAATCAATCTTTTTTTTTTTTTTTGGCCTGTGGGGACATTTTGTT  194
7R   GC-GAAGACTACATAATCAATCTTTTTTTTTTTTTTT-GGCCTGTGGGGACATTTTGTT  201
11   GC-GAAGACTACATAATCAATCTTTTTTTTTTTT----GGCCTGTGGGGACATTTTGTT  234
27R  ACAGAATACTATATACATAATACAAACAAATA-------AATAAATAAGTAAATATTATT  232
13   ACAGAATACTATATACATAATACAAACAAATA-------AATAAATAAGTAAATATTATT  233
      *  ***  ****  ***     ***        *            *    *  **  **  **

21   CAAACCATCC--CAGTGTGTGTGTGTGTGTGTGTGTGTGAGAGAGAGAGAGAGAGA  254
50   CAAACCATCC--CAGTGTGTGTGTGTGTGTGTGTGTGTGAGAGAGAGAGAGAGAGA  252
7R   CAAACCATCC--CAGTGTGTGTGTGTGTGTGTGTGTGTGAGAGAGAGAGACAG-----  254
11   CAAACCATCC--CAGTGTGTGTGTGTGTGTGTGTGTGTGAGAGAGAGAGACAGAGAGA  292
27R  AAAGGTGTGTGTCACCATGTCTGGCAATAATCATGTCCTTTTGTAATATTTACTTTGTGT  292
13   AAAGGTGTGTGTCACCATGTCTGGCAATAATCATGTCCTTTTGTAATATTTACTTTGTGT  293
      **    *    **  ***  **      *    ***    *    *    *    *
```

Fig 10

CLUSTAL W (1.83) multiple sequence alignment-Lineage 2

```
8     --------------------------------------------------TGCAGAGAT    9
42    --------------------------------------------------TTGGAGAGAT  10
37    --------------------------------------------------TTGGAGAGAT  10
26    --------------------------------------------------TTTGGAGAGAT 11
22    AGGGAAAGCTTGCATGCAGGCCTCTGCAGTCGACGGGCCCGGGATCCGATTTGGAGAGAT  60
                                                        *********

8     GGCTCGAGGTTAAGAGCACTGGCTGCTCTTCTAGAGGACAGGATTCAAATCCCAGCACTC  69
42    GGCTCGAGGTTAAGAGCACTGGCTGCTCTTCTAGAGGA AGGATTCAAATCCCAGCACTC  69
37    GGCTCGAGGTTAAGAGCACTGGCTGCTCTTCTAGAGGA-AGGATTCAA-TCCCAGCACTC  68
26    GGCTCGAGGTTA-GAGCACTGGCTGCTCTTCTAGAGGA-AGGATTCAA-TCCCAGCACTC  68
22    GGCTCGAGGTTAAGAGCACTGGGCTGCTCTTCTAGAGGACAGGATTCAAATCCCAGCACTC 120
      *********** ***************************** ******** **********

8     ACATGGTAGGTCACAACTCTCTGTAACCCAGGGGATCCAACACCCTCACATAGACATTCA 129
42    ACATGGTAGGTCACAACTCTCTGTAACCCAGGGGATCCAACACCCTCACATAGACATTCA 129
37    ACATGGTAGGTCACAACTCTCTGTAACCCAGGGGATCCAACACCCTCACATAGACATTCA 128
26    ACATGGTAGGTCACAACTCTCTGTAACCCAGGGGATCCAACACCCTCACATAGACATTCA 128
22    ACATGGTAGGTCACAACTCTCTGTAACCCAGGGGATCCAACACCCTCACATAGACATTCA 180
      ************************************************************

8     TGCAGGCAAAACATTGCACATAAAATTAAGTTTAAAAACAAAACAGGAATCCCAGACTGA 189
42    TGCAGGCAAAACATTGCACATAAAATTAAGTTTAAAAACAAAACAGGAATCCCAGACTGA 189
37    TGCAGGCAAAACATTGCACATAAAATTAAGTTTAAAAACAAAACAGGAATCCCAGACTGA 188
26    TGCAGGCAAAACATTGCACATAAAATTAAGTTTAAAAACAAAACAGGAATCCCAGACTGA 188
22    TGCAGGCAAAACATTGCACATAAAATTAAGTTTAAAAACAAAACAGGAATCCCAGACTGA 240
      ************************************************************

8     ATCTTTAAAAAGAAAGAAAAGAAAAAGAAAATGCCTTCCAGTTGGTTAAGGTTGGTTAC  249
42    ATCTTTAAAAAGAAAGAAAAGAAAAAGAAAATGCCTTCCAGTTGGTTAAGGTTGGTTAC  249
37    ATCTTTAAAAAGAAAGAAAAGAAAAAGAAAATGCCTTCCAGTTGGTTAAGGTTGGTTAC  248
26    ATCTTTAAAAAGAAAGAAAAGAAAAAGAAAATGCCTTCCAGTTGGTTAAGGTTGGTTAC  248
22    ATCTTTAAAAAGAAAGAAAAGAAAAAGAAAATGCCTTCCAGTTGGTTAAGGTTGGTTAC  300
      ************************************************************

8     AGTGCCCTTGTATCTCTGTATTGTAATAGCCTTTAAACCCTTCAAAGTATGTGCCATTTT 309
42    AGTGCCCTTGTATCTCTGTATTGTAATAGCCTTTAAACCCTTCAAAGTATGTGCCATTTT 309
37    AGTGCCCTTGTATCTCTGTATTGTAATAGCCTTTAAACCCTTCAAAGTATGTGCCATTTT 308
26    AGTGCCCTTGTATCTCTGTATTGTAATAGCCTTTAAACCCTTCAAAGTATGTGCCATTTT 308
22    AGTGCCCTTGTATCTCTGTATTGTAATAGCCTTTAAACCCTTCAAAGTATGTGCCATTTT 360
      ************************************************************

8     AAAATTCTAAAATCAAAGGCCAGAGAGAGAGAGAGAGAGAGAGAG-------------- 356
42    AAAATTCTAAAATCAAAGGCCAGAGAGAGAGAGAGAGAGAGAGAGAGAGAGAGAGAGAGA 369
37    AAAATTCTAAAATCAAAGGCCAGAGAGAGAGAGAGAGAGAGAGAGAGAGAGAGAGAGAGA 368
26    AAAATTCTAAAATCAAAGGCCAGAGAGAGAGAGAGAGAGAGAGAGAGAGAGAGAGAGA-- 366
22    AAAATTCTAAAATCAAAGGCCAGAGAGAGAGAGAGAGAGAGAGAGAGAGAGAGAGAGAGA 420
      *********************************************
```

SEQ ID NO:43:
GCTGGAGAGATGGCTCGAGGT TAAGAGCACTGGCTGCTCTTCCAGAGGTCCTGAGTCAATTCCCAGCAACCACATGGT

Complimentary strand of SEQ ID NO:9 (SEQ ID NO:44):
CGACCTCTCTACCGAGCTCCAATTCTCGTGACCGACGAGAAGGTCTCCAGGACTC AAGTTAAGGGTCGTTGGTGTACCA

Fig 14

```
CLUSTAL W (1.83) multiple sequence alignment

20GBP       GCTGGAGAGATGGCTCGAGGTTAAGAGCACCGACTGCTCTTCCAGAGGTCCTGAGTTCAATT    62
US6         GCTGGAGAGATGGCTCGAGGTTAAGAGCACTGACTGCTCTTCCAGAGGTCCTGAGTTCAATT    62
2FG         GCTGGAGAGATGGCTCGAGGTTAAGAGCACTGACTGCTCTTCCAGAAGTCCTGAGTTCAATT    62
49          GCTGGAGAGATGGCTCGAGGTTAAGAGCACTGGCTGCTCTTCCAGAGGTCCTGAGTTCAATT    62
US8         GCTGGAGAGATGGCTCGAGGTTGAGAACACTGGCTGCTCTTCCAGAGGTCCTGAGTTCAATT    62
5RP1        GCTGGAGAGATGGCTCGAGGTTAAGAGCACTGGCTGCTCTTCTAGAGGACA-GGATTCAATT    61
6RP2        GCTGGAGAGATGGCTCGAGGTTAAGAGCACTGGCTGCTCTTCCAGAGGTCTTGAATTCAATT    62
            ********************* *** *** * ******** ***  *  *  * ******

20GBP       CCCAGCAACCA------     73
US6         CCCAGCAACCA------     73
2FG         CCCAGCAACCA------     73
49          CCCAGCAACCA------     73
US8         CCCAGCAACCA------     73
5RP1        TCCAGCAACAACATGGT     78
6RP2        TCCAGCAACAACATGGT     79
            ********  *
```

Fig 15

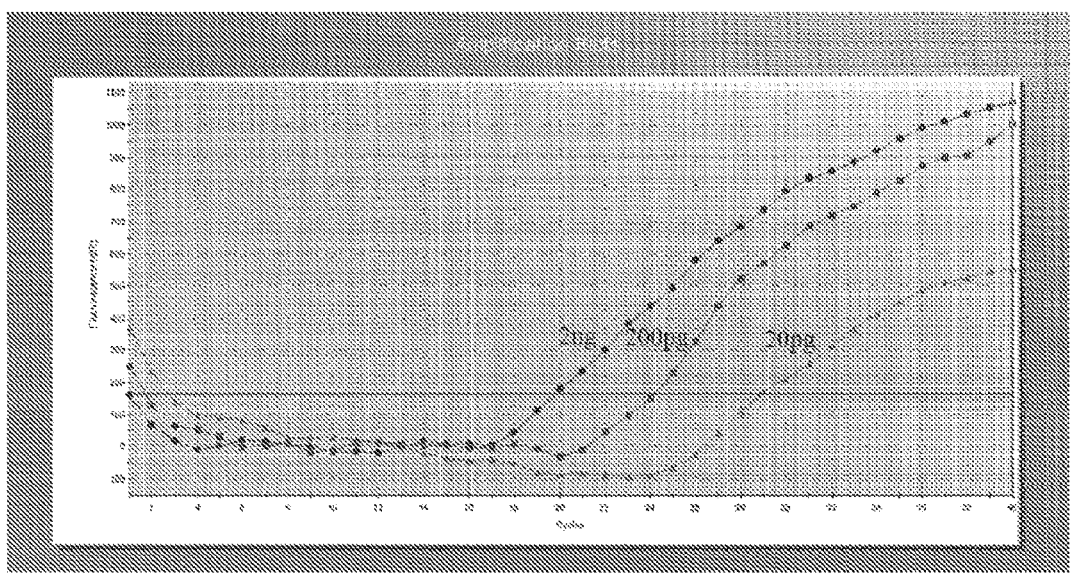

Fig 16

SEQ ID NO:1:

GCTGGAGAGATGGCTCGAGGTTAGAGCACTGGCTGCTCTTCCAGAGGTCCTGAGTTCAATTCCCAGCAACCAC

Complementary strand of SEQ ID NO:1 (SEQ ID NO:45):

CGACCTCTCTACCGAGCTCCAATTCTCGTGACCGACGAGAAGGTCTCCAGGACTCAAGTTAAGGGTCGTTGGTG

Fig 17

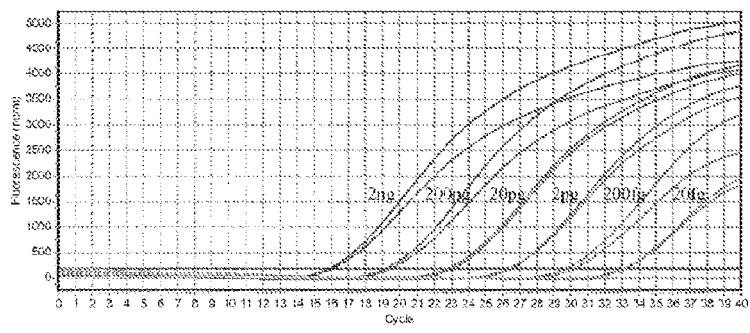

Threshold: 176 (Noiseband)
Baseline settings: automatic, Drift correction OFF

Fig 18a

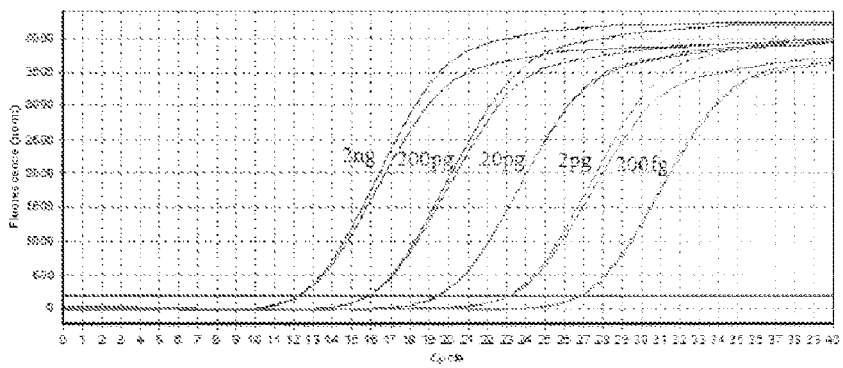

Threshold: 197 (Adjusted manually)
Baseline settings: automatic, Drift correction ON Threshold: 33%

Fig 20

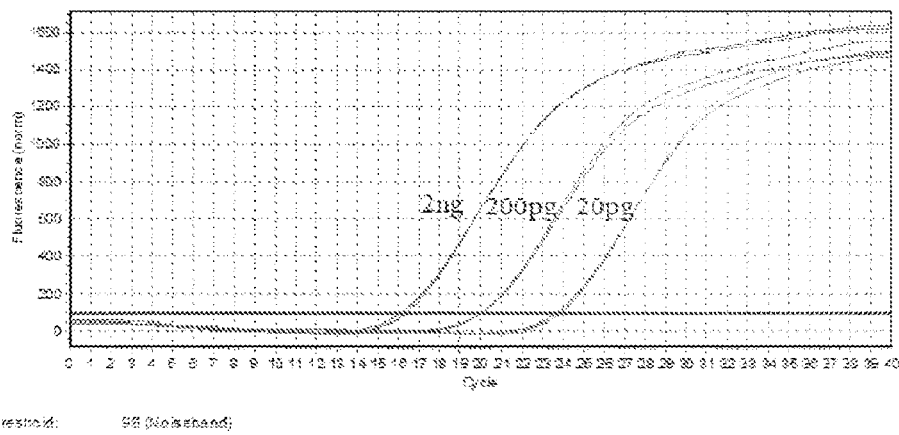

Threshold: 96 (Noiseband)
Baseline settings: automatic Drift correction OFF

Fig 21a

```
Seq27    CATTGGTGGCACACACCTTTAATCCCAGCACTCGGGAGGCAGAGGCAGGTGGATCTCTGT 60
Seq1     -GCTGGAG--AGATGGCTCGAGGTTAAGAGCACTGACTGCTCTCCAG--AGGTCC---T 52
          ***   *    *  *   **   *    **   *   **    ***   ***   *

Seq27    GAGTTCAAGAGCCAGC---CTGG 90
Seq1     GAGTTCAATTCCAGCAACCAC 74
         ********  *****  *
```

Fig 21b

```
SEQ28    CCAGGCATTGGTGGCACACACCTTTAGTCCCAGCACTCAGGAGGCAGAGGCAGGAG--GAT 59
SEQ1     ---------------------------------------------GCTGGAGAGAT 11
                                                      **  ****  ***

SEQ28    CACTTGAGTTCAAGAGC-CAGCCTGGTCTACCAGAGTCCCTGAGTTCAAGCCAGCCTATA 118
SEQ1     GGCTCGAGGTTAAGAGCACTGACTGCTCTTCCAGAGGTCCTGAGTTCAA--------TT 62
           **  *** *  ****** *  *   *** ***  ***** **********      *

SEQ28    CAGAGAAACCCTGTCT 134
SEQ1     CCCAGCAACCAC---- 74
          *  ** ****
```

Fig 22a

```
Identities = 76/80 (95%), Gaps = 1/80 (1%)
 Strand=Plus/Plus

SeqID27  1   CATTGGTGGCACACACCTTTAATCCCAGCACTCGGGAGGCAGAGGCAGGTGGATCTCTGT   60
             |||||||||||||| |||||||||||||||||||||||||||||||||| ||||||||||
Sbjct   26   CATTGGTGGCACACTCCTTAATCCCAGCACTCGGGAGGCAGAGGCAGGCGGATCTCTGT   85

SeqID27  61  GAGTTCAAGAGCCAGCCTGG   80
             |||||| || |||||||||||
Sbjct   86  GAGTTCGAG-CCAGCCTGG    104
```

Fig 22b

```
Identities = 110/140 (79%), Gaps = 10/140 (7%) Strand=Plus/Minus

SeqID28  1   CCAGGCATTGGTGGCACACACCTTTAGTCCCAGCACTCAGGAGGCAGAGGCAGGAGGATC
60
             ||||||||||||||||||||||||||||||||||||||   | ||||||||||||  ||
Sbjct   149  CCAGGCATTGGTGGCACACACCTTTAGTCCAGCAAGTGGAAGGCAGAGGCAGGCAAAT-   91

SeqID28  61  ACTTG--AGTTCAAGAGCCAGCCTGGTCTAC-CAG--AGTTCCTGAGTTCAAGCC-AGGC   114
             |||    ||| |||| ||||||||||||||  ||  || ||  | |   ||  |||||
Sbjct   90   --TTGTAAGTACAAG-GCCAGCCTGGTCTACAGAGTAAGTGCCAGGATACGCTCCAAAGC   34

SeqID28  115 TATACAGAGAAACCCTGTCT   134
             || ||||||||||||||||||
Sbjct   33   TACACAGAGAAACCCTGTCT   14
```

Fig 23a

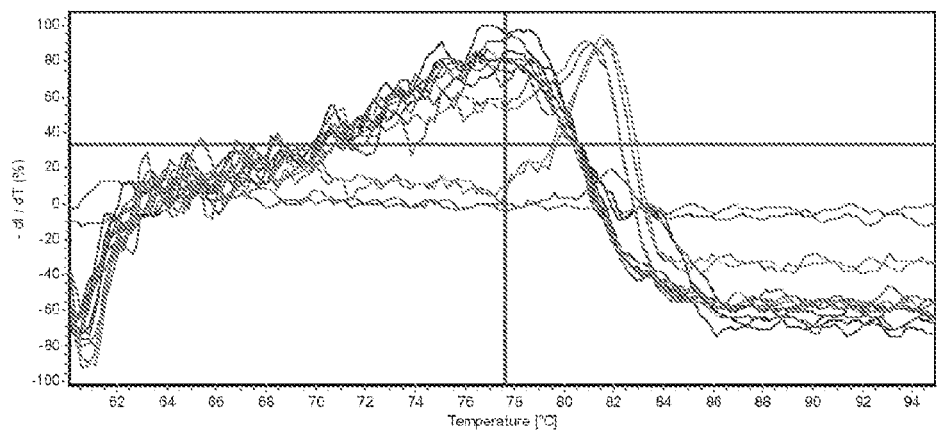

Threshold: 33%

Threshold: 33%

Threshold: 33%

Fig 24b

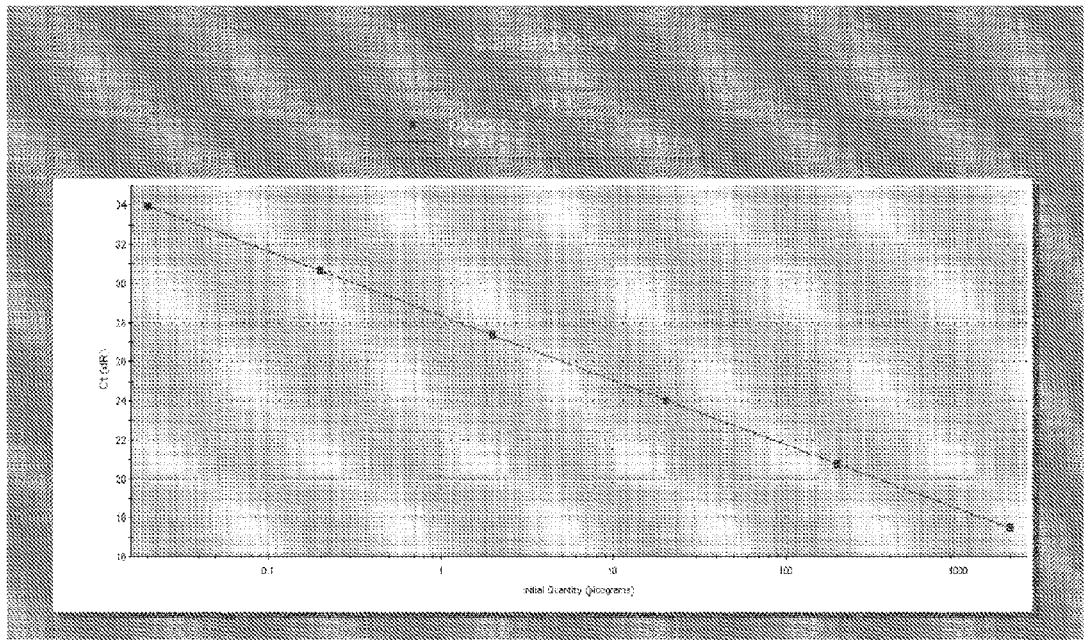

Fig 25

```
SeqID1    GCTGGAGAGATGGCTCGAGGTAAGAACACTGACTGCTCT-T-CCAGAGGTCTGAGTTC
58
XS01      GCTGGAGAGATGGCTCGAGGTGAGAACATGACTGCTCT-T-CCAGAGGTCTGAGTTC
58
XS02      GCTGGAGAGATGGCTCGAGGTAAGAACACTGACTGCTCT-TTCCGAAGGTCTGAGTTC
59
XS03      -CTGGAGAGATGGCTCGAGGTAAAAACACTGACTGTTCTCTTCCGGAAGTTCTGAGTTC
59
XS04      -CTGGAGAGATGGCTCGAGGTAAAAACACTGACTGTTCTCTTCCGGAAGTTCTGAGTTC
59
          *********** *********  *  * *** *** ***  *  **   *  *  *********

SeqID1    AATTCCCAGCAACCAC  74
XS01      AATTCCCAGCAACCA-  73
XS02      AATTCCCAGCAA----  71
XS03      AATTCCCAGCAACCAC  75
XS04      AATTCCCAGCAACCAC  75
          ************
```

METHOD OF DETECTING RESIDUAL GENOMIC DNA AND A KIT THEREOF

PRIORITY APPLICATIONS

This application is a U.S. National Stage Filing under 35 U.S.C. 371 from International Application No. PCT/IB2012/051046, filed on 6 Mar. 2012, and published as WO 2013/108083 A1 on 25 Jul. 2013, which claims the benefit under 35 U.S.C. 119 to Indian Application No. 164/CHE/2012, filed on 16 Jan. 2012; which applications and publication are incorporated herein by reference in their entirety.

TECHNICAL FIELD

The present disclosure describes a sensitive method of determining and detecting residual DNA in a biological sample wherein specific region of Alu equivalent sequences in Chinese Hamster Ovary (CHO) genomic DNA is detected with the help of designed primers and probe. The designed probe helps in increasing the sensitivity as well as the accuracy of the method. Hence the identification of specific regions within the CHO genomic DNA increases the overall sensitivity and efficiency of the detection process.

BACKGROUND AND PRIOR ART OF THE DISCLOSURE

Biopharmaceuticals are medical drugs produced using biotechnology. They include proteins (including antibodies), nucleic acids (DNA, RNA or antisense oligonucleotides) and living microorganisms like virus and bacteria where the virulence of viruses and bacteria is reduced by the process of attenuation. They can be used for therapeutic or in vivo diagnostic purposes, and are produced by means other than direct extraction from a native (non-engineered) biological source.

The removal of host cell impurities is a critical step in the production of biopharmaceutical products. One impurity targeted for clearance during the purification process is residual DNA arising from host cells. Traditional methods of quantitating residual host cell DNA have been limited by laborious sample preparation protocols, lack of sensitivity and specificity, and slow time to results.

In the process of manufacturing biopharmaceuticals, strict guidelines need to be followed to ensure the final pharmaceutical formulations are free of impurities and meet the regulatory guidelines. Among the common impurities are host cells which need to be removed before the final formulation. Majority of the therapeutic proteins are expressed using recombinant technology in the cell lines derived from the rodent family. The purified protein from the bulk harvest is likely to carry traces of CHO host cell genomic DNA into the final formulation thereby posing additional risk. Therefore, regulatory agencies like the world health organization (WHO), European Medicine Agency (EMA) or Food and Drug Administration (FDA) have documented the permissible levels of host cell DNA per dose of the drug administered to the patients in the guidelines. The present disclosure discloses a method of early detection and quantification of host cell genomic DNA contamination using a quantitative real time PCR.

In addition to potential safety issues stemming from the presence of extraneous host cell DNA, the regulatory guidance for products produced in cell culture is that DNA content in the final product should be as low as possible, as determined by a highly sensitive method. Traditional methods of quantifying levels of residual host cell DNA have been limited by lack of sensitivity and specificity, poor assay reliability, low sample capacity, slow time-to-results and high cost per sample tested.

Residual DNA in final bulk products should be generally lower than 100 pg per therapeutic dose (*Points to consider in the manufacture and testing of monoclonal antibody products for human use*, Centre for Biologics Evaluation and Research, US food and drug administration; 28 Feb., 1997; www.fda.gov/cber/gdlns/ptc_mab.pdf). The FDA also recommends that detection methods used be sensitive enough to detect residual amounts present in picogram levels. Three techniques have the required sensitivity to detect picogram levels of impurities: hybridization, methods based on DNA-binding protein and quantitative PCR (q-PCR).

Goldman et al. (Clinical chemistry 37:1523, 1991) describes a method of determining levels of DNA contamination using polymerase chain reaction. However, the methods described here are not sensitive enough to detect contamination in picogram levels. U.S. Pat. No. 5,393,657 discloses the use of primers and PCR amplification to detect the presence of host cell DNA contamination. However, conventional molecular biology techniques such as Southern blotting and gel electrophoresis are used for detection and quantification of the impurities. This reduces the overall ease of operation as well as the sensitivity.

U.S. Patent application No. 2009/0325175 discloses a method of identifying host cell genomic DNA contamination utilizing quantitative real time Polymerase chain reaction, wherein the qPCR primers are complementary to the highly repetitive host cell genomic DNA sequences, e.g. Alu-equivalent sequences. The cited document does not talk about the specific 74 bp Alu consensus sequence for which the instant disclosure become more sensitive. Therefore, a process which increases specificity and sensitivity in detecting the presence of host cell contamination is required. The present disclosure can detect the residual DNA impurities from the host cell of the rodent family as low as 20 femtogram in a recombinant protein product by using specific primers and probe.

STATEMENT OF DISCLOSURE

Accordingly, the present disclosure relates to a sensitive and quantitative method to detect the residual genomic DNA from a host cell of rodent family as low as 20 femtogram in a protein product by using primer sequence ID number 22 and sequence ID number 23 and corresponding probe sequence ID number 24 targeted to amplify Alu family of the dispersed sequences; and a kit for detecting and optionally quantifying residual genomic DNA having an Alu sequence, from a biological sample containing a protein product, said kit comprising the primer as claimed in claim 18, the probe as claimed in claim 20 and quantitative real-time PCR reagents, optionally along with an instruction manual.

BRIEF DESCRIPTION OF ACCOMPANYING FIGURES

The following description gives examples of embodiments of the present disclosure and is made with respect to the attached Figures in a purely exemplifying and non limiting manner, wherein:

FIG. 1: Represents the alignment of five cloned Alu-equivalent sequences designated as 2FG (Seq ID no 2), US15 (SEQ ID no 3), 200PG (Seq ID no 4), US6 (SEQ ID no 5) and US8 (SEQ ID no 6) obtained from CHO genomic DNA used. The consensus sequence mentioned as BioAlu in the alignment is represented as SEQ ID no 1. The similarity in the aligned sequences is represented by asterisk sign at the bottom row of the alignment.

FIG. 2a: Represents the amplification plots of the standard CHO DNA dilutions starting from 2 ng, 200 pg and 20 pg.

FIG. 2b: Represents the melting curve of the PCR product formed with the use of SEQ ID nos. 7 and 8 with the CHO genomic DNA.

Figure 3:
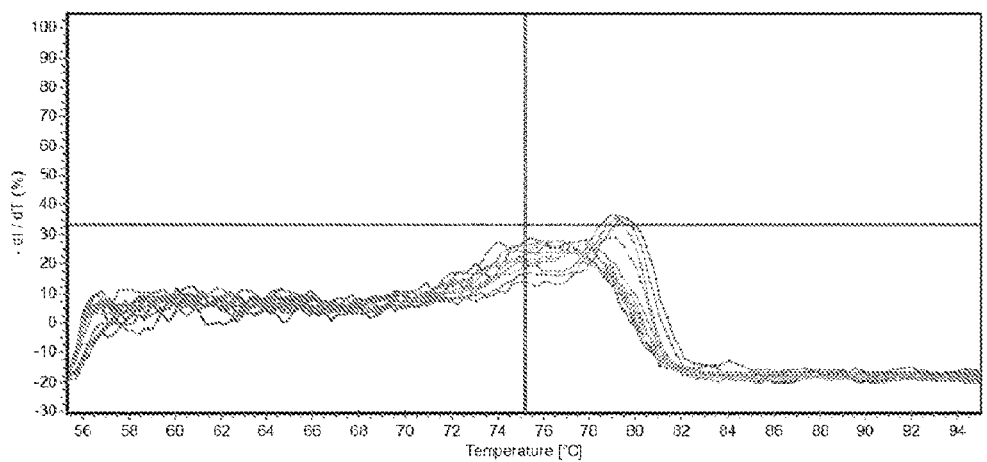

FIG. 3: Represents the melt curve analysis of the gradient qPCR to optimize the annealing temperature.

Figure 4A:
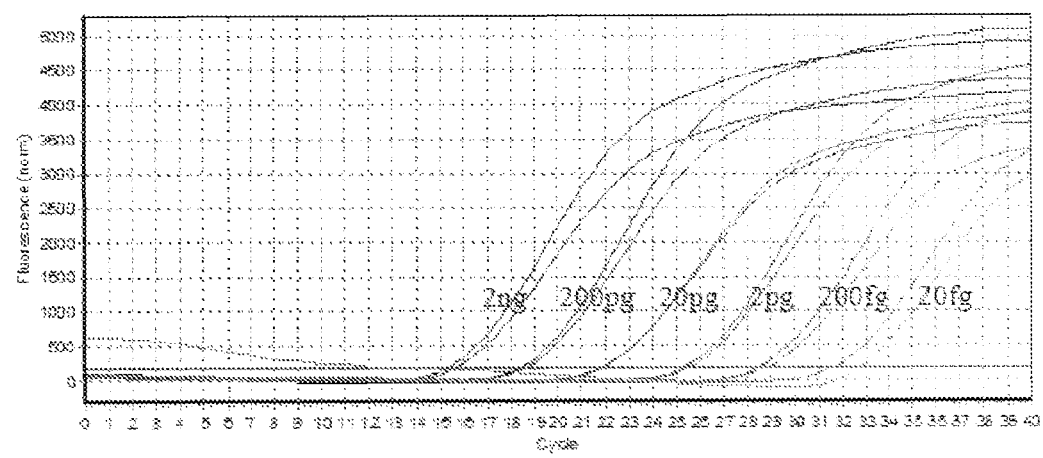

FIG. 4a: Represents the amplification plots of standard CHO DNA dilutions-2 ng, 200 pg, 20 pg, 2 pg, 200 fg and 20 fg obtained with optimized concentration of primers (400 nM) and at optimized annealing temperature (64° C.). The plots look linear and sigmoid.

Figure 4B:
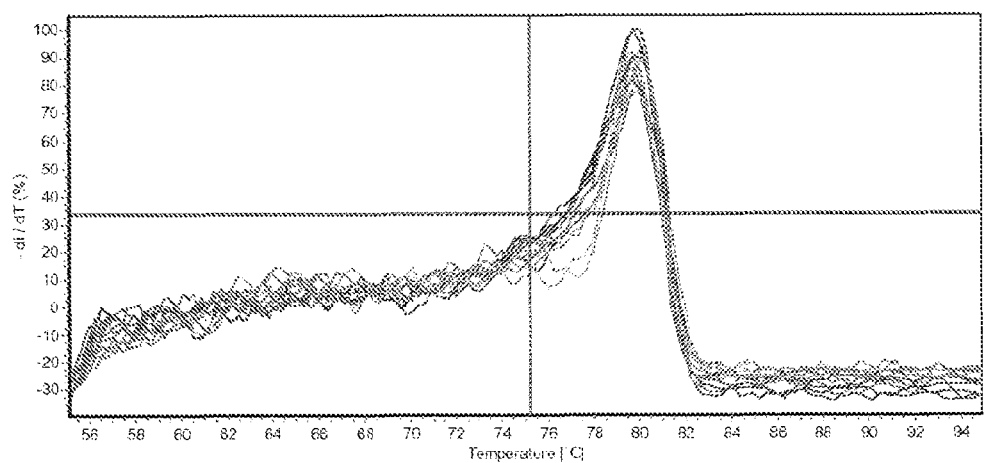

FIG. 4b: Represents the melting curve obtained from the PCR product amplified from the standard DNA dilutions using optimized primer and annealing temperature for the reaction. The melting curve obtained is tapering having a sharp peak which is indicative of specific amplification of the target.

Figures 5, 6A:
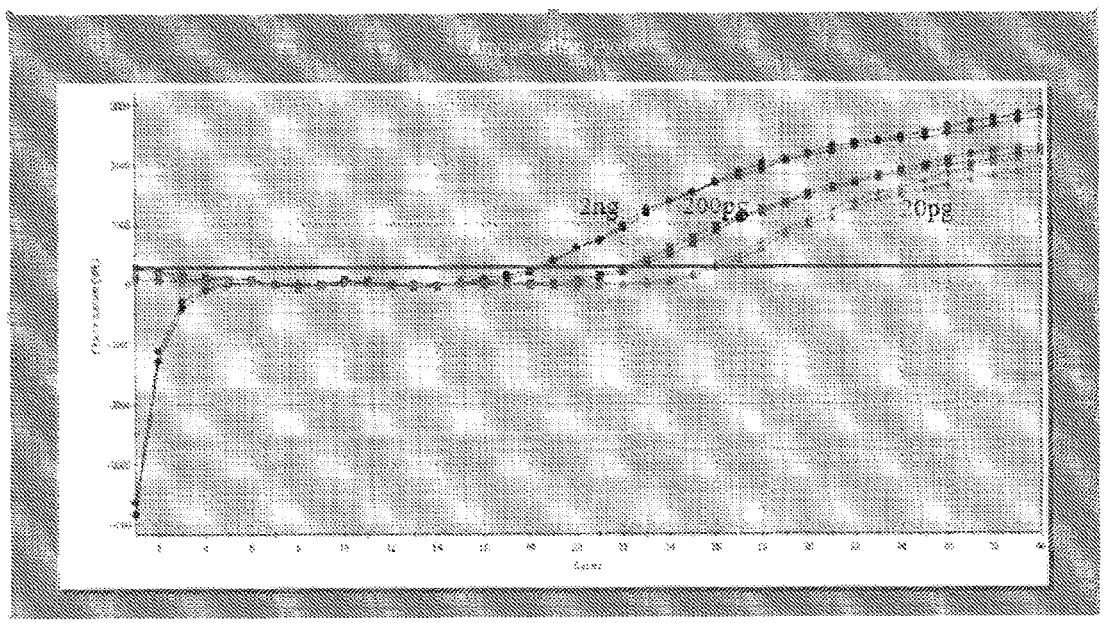

FIG. 5: Represents the SEQ ID no 9 obtained from target amplified from the CHO genomic DNA using primers SEQ ID no 7 and 8. The length of the sequence is found to be 71 bp.

FIG. 6a: Represents the amplification plots obtained by using the Taqman probe SEQ ID no 10.

Figures 6B, 7:
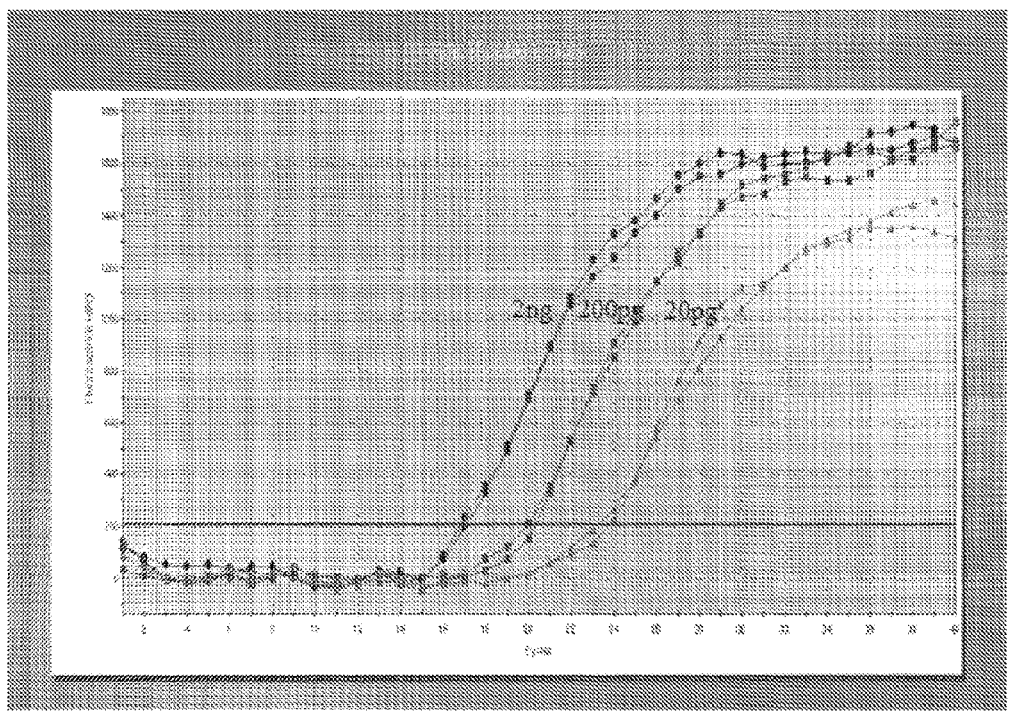

FIG. 6b: Represents the forward and reverse primer binding regions to the SEQ ID no 9, designated as SEQ ID nos. 11 and 12 respectively.

FIG. 7: Represents the amplification plots obtained by using the qPCR primer SEQ ID no 11 and 12 and qPCR probe SEQ ID no 10. The plots are wavy indicating that the probe binding efficiency is poor.

Figures 8A, 8B:
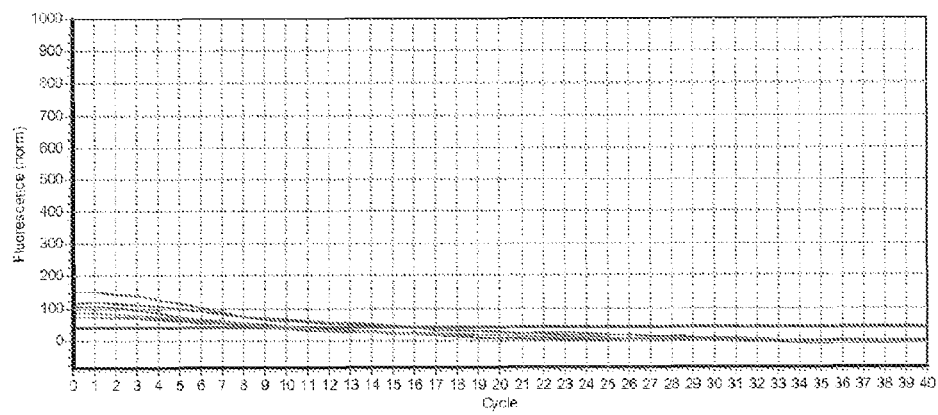

FIG. 8a: Represents the forward and reverse primers designated as SEQ ID nos. 14 and 15 respectively, binding regions to the Seq ID no. 9.

FIG. 8b: Represents the inefficient binding of primers/probe to the target indicated by no rise in amplification plots.

FIG. 9: Represents the lineage 1 of the Alu-equivalent sequence (SEQ ID NOs: 32 to 37). The highlighted region is the reverse primer designated as SEQ ID NO: 17 using online software.

FIG. 10: Represents the lineage 2 of the Alu-equivalent sequence (SEQ ID NOs: 38 to 42). The highlighted region is the reverse primer designated as SEQ ID NO: 18 using online software.

Figures 11, 12:
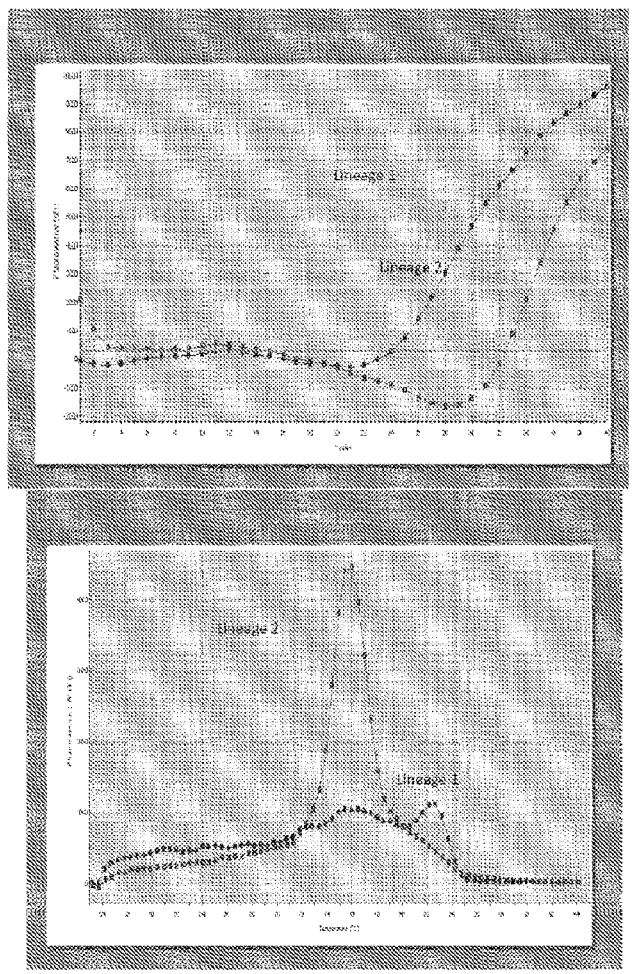

FIG. 11: Represents the amplification plots and melting curve obtained by using the primers of SEQ ID NO: 17 and 18.

FIG. 12: Represents the redesigned forward and reverse primers designated as SEQ ID NOs: 19 and 20 respectively, which are shown as highlighted on SEQ ID NO: 43 and 44.

Figure 13A:
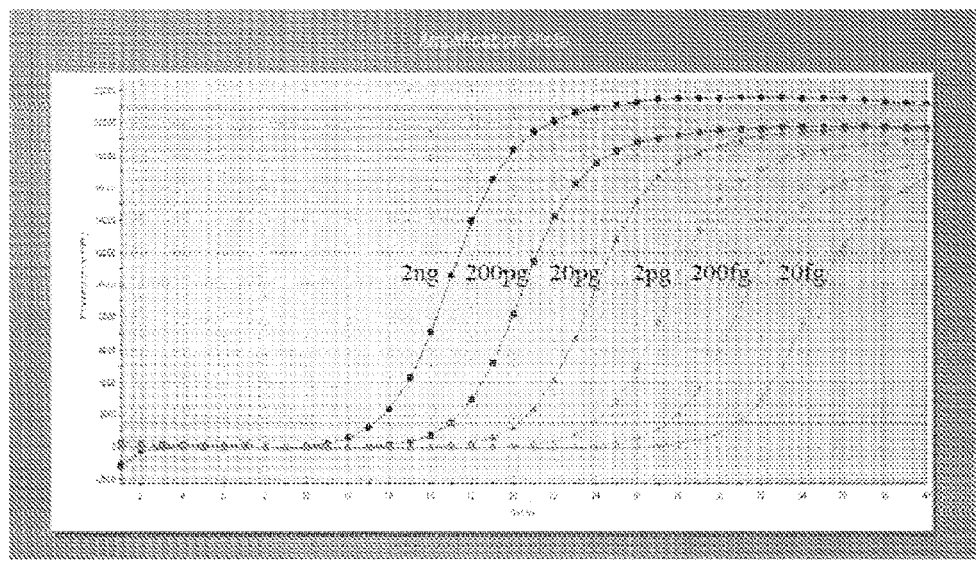

FIG. 13a: Represents the amplification of CHO standard DNA dilutions from 2 ng to 20 fg using the SEQ ID no 19 and 20.

Figure 13B:
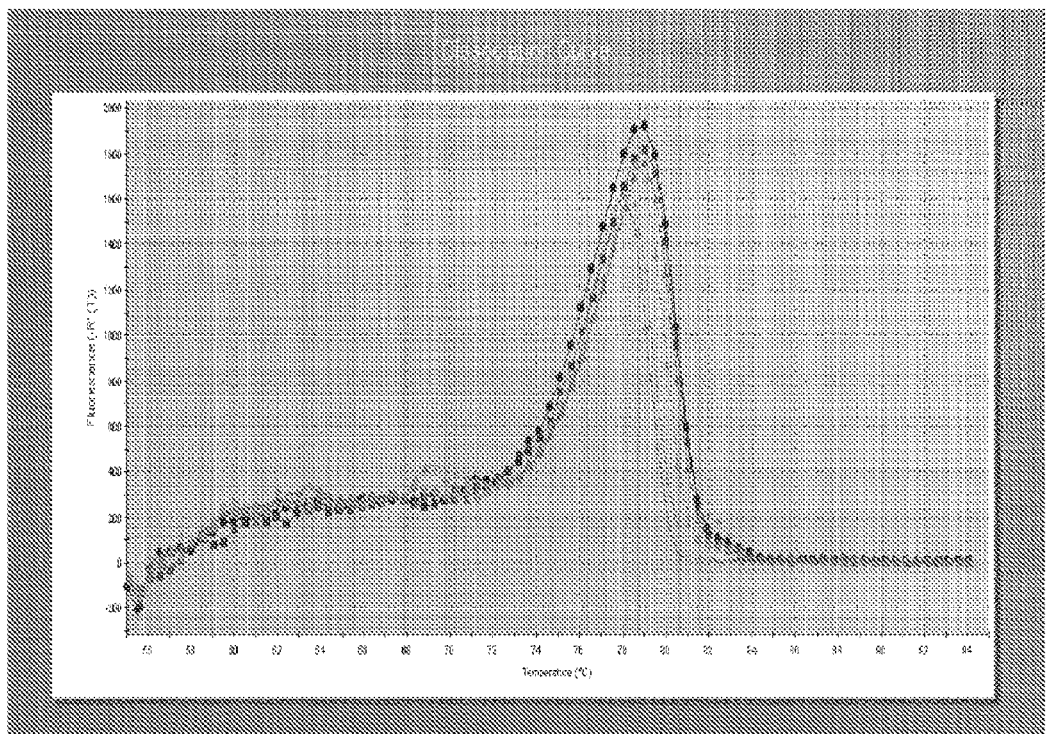

FIG. 13b: Represents the melting curve of the PCR product formed using the seq ID nos 19 and 20.

FIG. 14: Represents the alignment of sequences (SEQ ID NOs: 46 to 52) obtained from residual CHO DNA detected from downstream purification process samples using SEQ ID NOs: 19 and 20.

FIG. 15: Represents the amplification plots of 3 standard DNA dilutions using the degenerate probe seq ID no 21 and qPCR primer SEQ ID no 19 and 20.

FIG. 16: Represents the redesigned forward and reverse primers designated as SEQ ID NOs: 22 and 23, respectively, which are shown as highlighted on the SEQ ID NO: 1.

FIG. 17: Represents the amplification plots obtained by using optimized concentration of qPCR primers of SEQ ID NO: 22 and 23 and degenerate probe of SEQ ID NO: 24.

FIG. 18a: Represents the amplification plots obtained by using optimized concentration of qPCR primers of SEQ ID NOs: 22 and 23 for the CHO standard DNA dilutions from 2 ng to 200 fg.

Figure 18B:
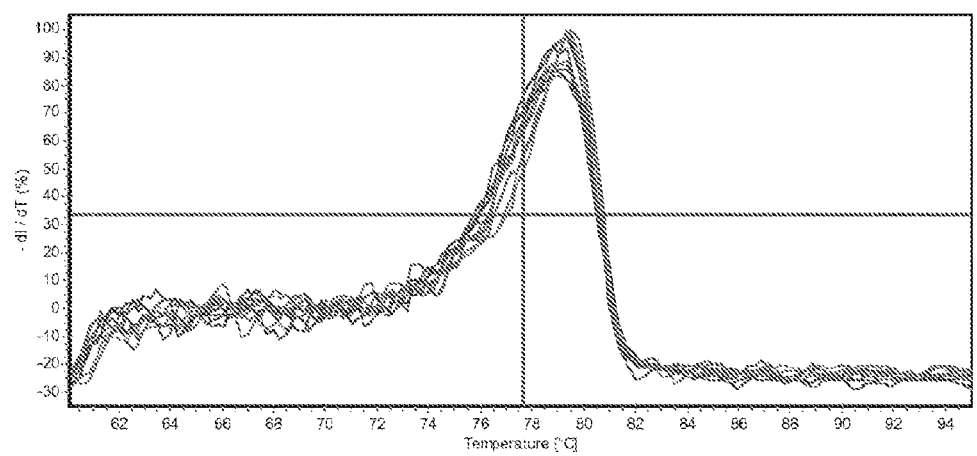

FIG. 18b: Represents the melting curve of the PCR product formed from using the SEQ ID nos 22 and 23.

Figure 19:
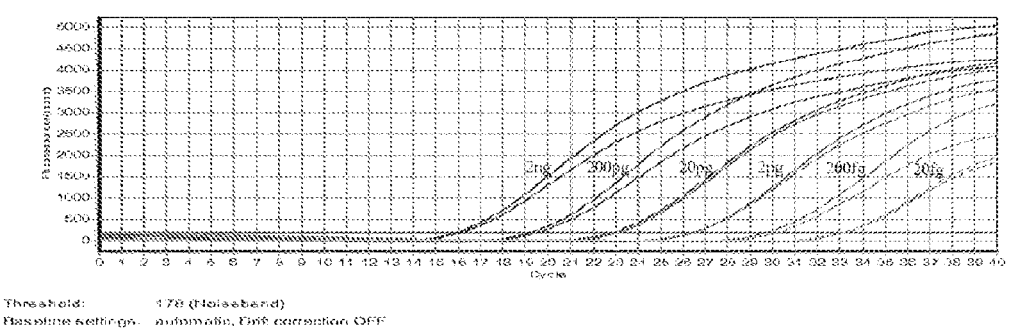

FIG. 19: Represents the amplification plots obtained by using optimized concentration of qPCR primers of SEQ ID NOs: 22 and 23 and degenerate probe SEQ ID NO: 24.

FIG. 20: Represents the amplification plots of standard DNA dilutions 2 ng, 200 pg and 20 pg with optimized concentrations of the primers (SEQ ID NOs: 22 and 23) and probe (SEQ ID NO: 24).

FIG. 21a: Represents the alignment of the Alu-equivalent sequence designated SEQ ID 1 and the published Alu sequence designated as SEQ27. The similarity in the aligned sequences is represented by asterisk sign at the bottom row of the alignment.

FIG. 21b: Represents the alignment of the Alu-equivalent sequence designated as SEQ ID 1 with the sequence designated as SEQ 28. The similarity in the aligned sequences is represented by asterisk sign at the bottom row of the alignment.

FIG. 22a: Represents the alignment of SEQ ID NO: 27 with the sequence that is identified using primers designated as SEQ ID 25 and SEQ ID 26 on CHO genomic DNA (represented as Sbjct; SEQ ID NO: 53). The alignment is done using BLAST online software.

FIG. 22b: Represents the alignment of SEQ ID NO: 28 with the sequence that is identified using primers designated as SEQ ID NO: 29 and SEQ ID NO: 30 on CHO genomic DNA (represented as Sbjct; SEQ ID NO: 54). The alignment is done using BLAST online software.

FIG. 23a: Represents the melting curve of the PCR amplified product from the primers designated as SEQ ID 25 and SEQ ID 26 with CHO DNA. The irregular pattern of the melting curve is indicative of high degeneracy existing within the sequence.

Figure 23B:
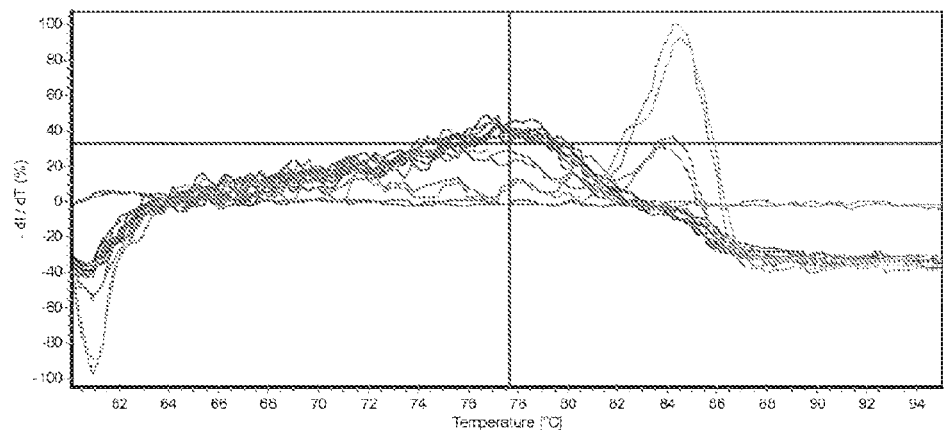

FIG. 23b: Represents the melting curve of the PCR amplified product from the primers designated as SEQ ID 29 and SEQ ID 30 with CHO genomic DNA. The irregular pattern of the melting curve indicates that the high degeneracy exists within the sequence.

Figure 23C:
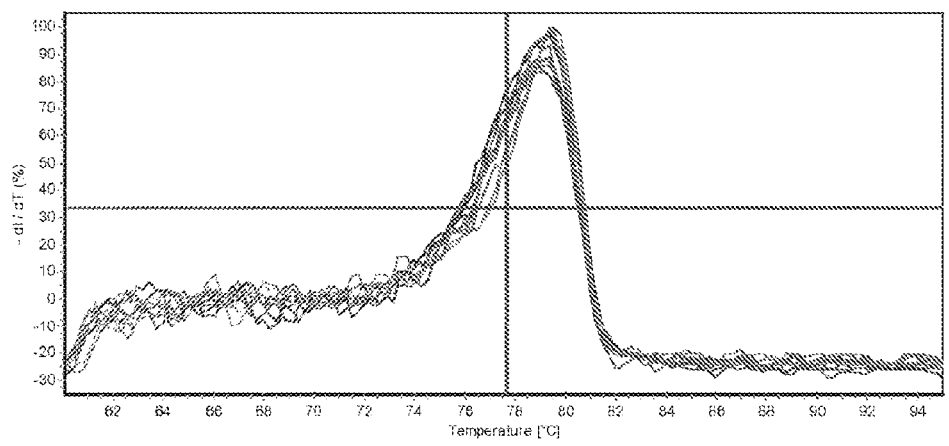

FIG. 23c: Represents the melting curve of the PCR amplified product from the primers SEQ ID 22 and SEQ ID 23 and CHO genomic DNA.

Figure 24A:
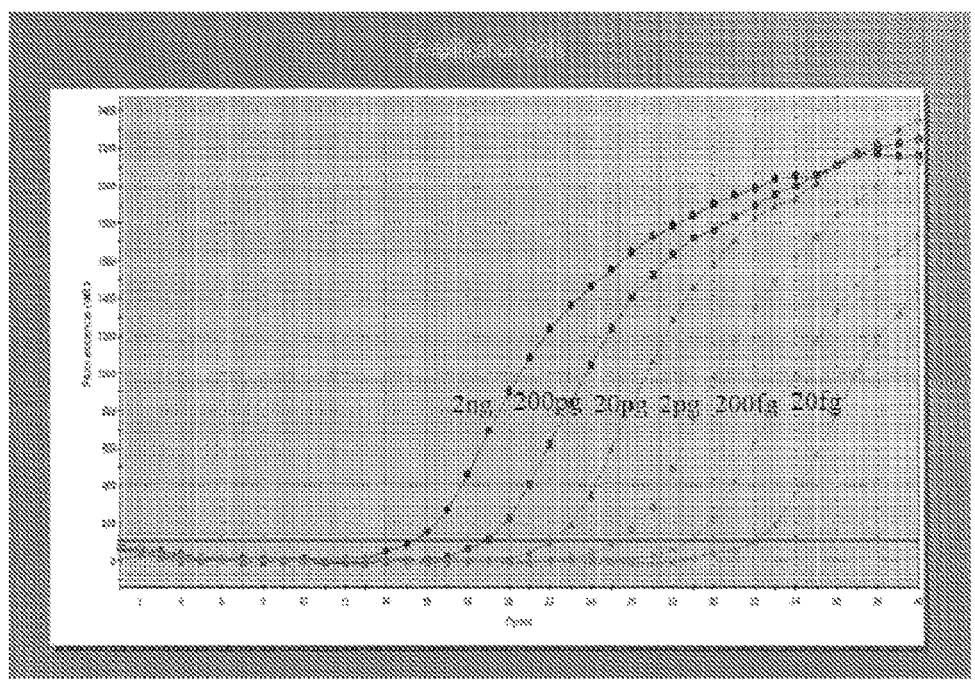

FIG. 24a: Represents the standard DNA dilution amplification plot obtained using the Taqman probe SEQ ID 24 and primers SEQ ID 22 and SEQ ID 23 and CHO genomic DNA.

FIG. 24b: Represents the standard curve of the CHO DNA dilutions from 2 ng to 20 fg using the SEQ ID 22 and SEQ ID 23 with its Taqman probe SEQ ID 24.

FIG. 25: Represents the sequence comparison of target (SEQ ID NO: 1) with the PCR product amplified from NSO genomic DNA using primers SEQ ID NOs: 22 and 23. (SEQ ID NOs: 55-58)

Figure 26:
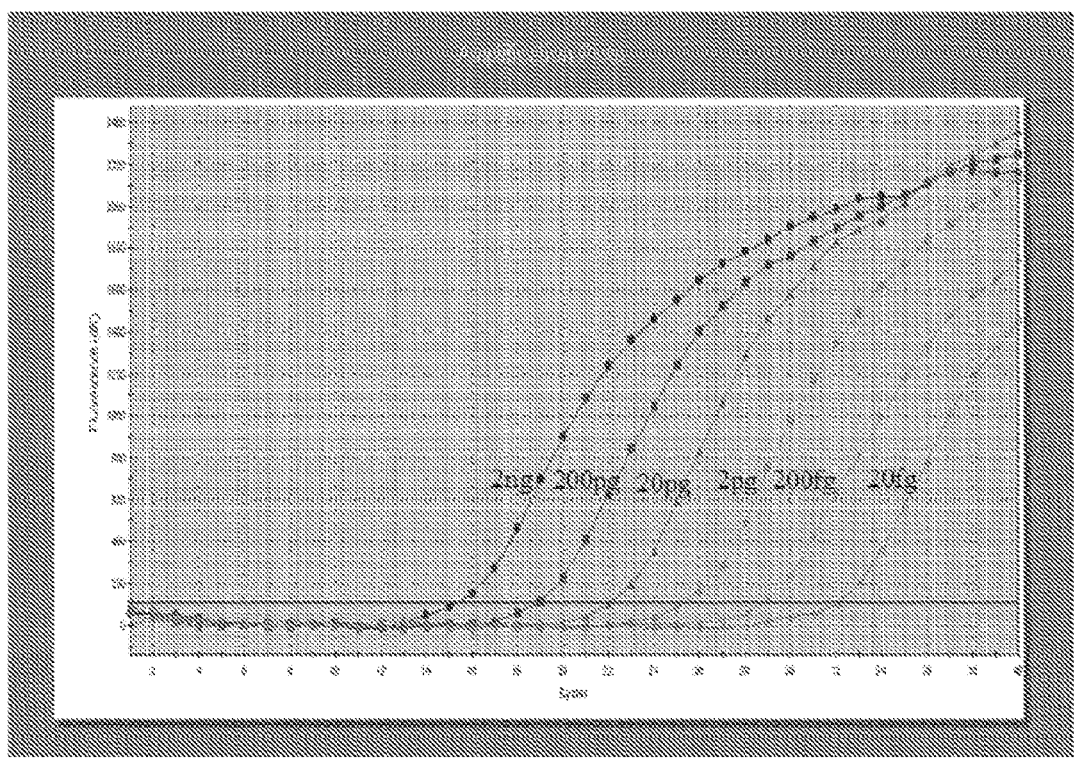

FIG. 26: Represents dynamic range and sensitivity. The figure represents the amplification plots generated from running the assay with a tenfold serial dilution from 2 ng to 20 fg of CHO genomic DNA, purified from CHO cell line producing therapeutic protein.

Figure 27:
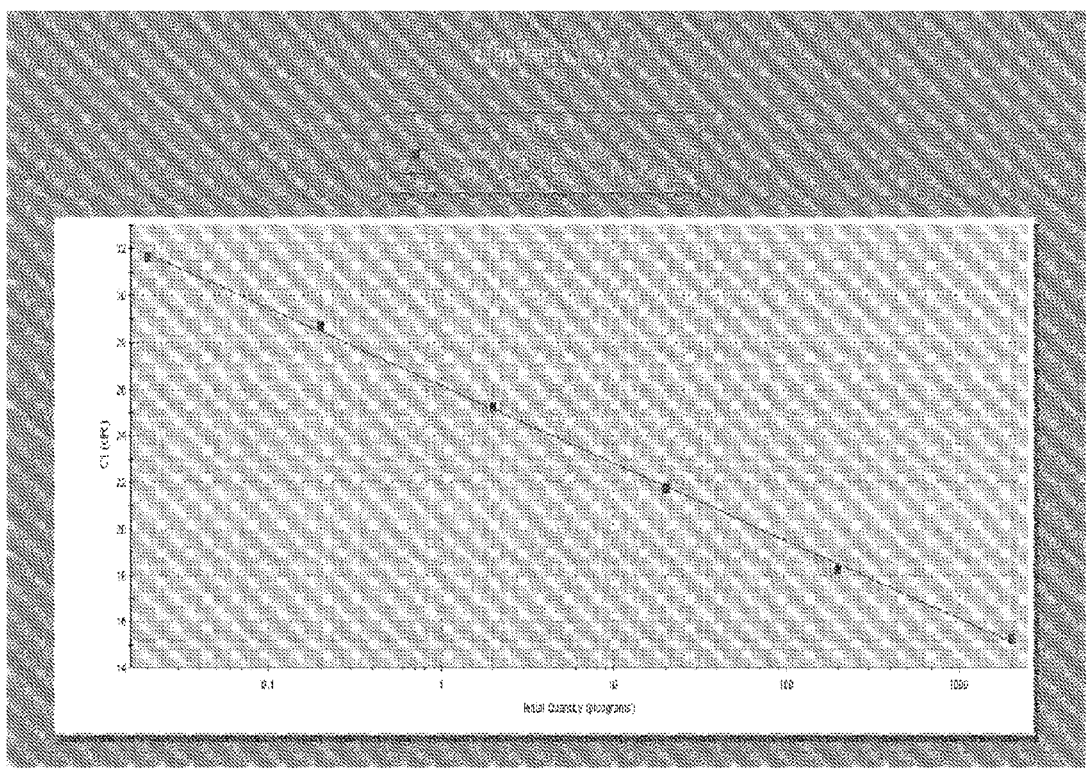

FIG. 27: Represents the standard curve of the CHO DNA dilutions from 2 ng to 20 fg along with the slope and correlation coefficient.

LIST OF PUBLISHED SEQUENCES AND CORRESPONDING PROBES AND PRIMERS

| SEQUENCE TYPE | SEQ ID No. (This application) | Corresponding published SEQ IDs. | Reference of published SEQ IDs. |
|---|---|---|---|
| Forward primer | SEQ NO. 25 | SEQ No. 2 | US20090325175 |
| Reverse primer | SEQ NO 26 | SEQ No. 3 | US20090325175 |
| Alu equivalent sequence | SEQ NO 27 | SEQ No. 9 | US20090325175 |
| Alu equivalent sequence | SEQ NO 28 | SEQ No. 1 | U.S. Pat. No. 5,393,657 |
| Forward primer | SEQ NO 29 | SEQ No. 2 | U.S. Pat. No. 5,393,657 |
| Reverse primer | SEQ NO 30 | SEQ No. 3 | U.S. Pat. No. 5,393,657 |

BRIEF DESCRIPTION OF ACCOMPANYING SEQUENCE LISTINGS

SEQ ID No 1 represents Alu equivalent consensus sequence

SEQ ID No 2 represents Alu equivalent sequence amplified from DNA obtained from downstream manufacturing step samples.

SEQ ID No 3 represents Alu equivalent sequence amplified from DNA obtained from downstream manufacturing step samples.

SEQ ID No 4 represents Alu equivalent sequence amplified from DNA obtained from downstream manufacturing step samples.

SEQ ID No 5 represents Alu equivalent sequence amplified from DNA obtained from downstream manufacturing step samples.

SEQ ID No 6 represents Alu equivalent sequence amplified from DNA obtained from downstream manufacturing step samples.

SEQ ID No 7 represents the forward qPCR primer

SEQ ID No 8 represents reverse qPCR primer

SEQ ID No 9 represents the sequence of the target obtained from the positive clone plasmid SEQ ID No 10 represents the Taqman qPCR probe.

SEQ ID No 11 represents redesigned forward primer

SEQ ID No 12 represents redesigned reverse primer

SEQ ID No 13 represents the sequence of the Taqman qPCR probe

SEQ ID No 14 represents the sequence of the new forward primer

SEQ ID No 15 represents the sequence of the new reverse primer

SEQ ID No 16 represents the sequence of the new Taqman probe

SEQ ID No 17 represents reverse primer

SEQ ID No 18 represents reverse primer

SEQ ID No 19 represents forward primer

SEQ ID No 20 represents reverse primer

SEQ ID No 21 represents the degenerate Taqman qPCR probe

SEQ ID No 22 represents the forward qPCR primer

SEQ ID No 23 represents the reverse qPCR primer

SEQ ID No 24 represents a new designed degenerate probe with 1 degenerate base.

SEQ ID No 25 represents the sequence of the published forward primer

SEQ ID No 26 represents the sequence of the published reverse primers

SEQ ID No 27 represents the sequence of the published Alu sequence

SEQ ID No 28 represents the sequence of the published Alu sequence

SEQ ID No 29 represents the published forward primer

SEQ ID No 30 represents the published reverse primer.

DETAILED DESCRIPTION OF THE DISCLOSURE

The present disclosure relates to a sensitive and quantitative method to detect the residual genomic DNA from a host cell of rodent family as low as 20 femtogram in a protein product by using primer sequence ID number 22 and sequence ID number 23 and corresponding probe sequence ID number 24 targeted to amplify Alu family of the dispersed sequences.

In an embodiment of the present disclosure, the technique for detecting residual genomic DNA from a mammalian host organism in a protein product, said method comprising steps of:
a. extracting DNA from the sample;
b. designing suitable primers to amplify a region of the CHO genomic DNA and designing a specific probe to anneal to a target sequence located between two PCR amplification primers;
c. amplifying the targeted sequences with the pair of specific primers and a DNA-based probe with a fluorescent reporter at one end and a quencher of fluorescence at the opposite end of the probe;
d. breakdown of the probe by the 5' to 3' exonuclease activity of the Taq polymerase breaks the reporter-quencher proximity and thus allows unquenched emission of fluorescence; and
e. the increase in fluorescence and accumulation of the PCR product is continually monitored throughout the PCR reaction by real-time PCR instrument.

Wherein the change of fluorescence in each cycle is proportional to the identification of specific amplified sequences and indicates the presence of residual genomic DNA in the sample.

In another embodiment of the present disclosure, the amplifying is carried out using quantitative real time PCR employing Taq DNA polymerase.

In yet another embodiment of the present disclosure, the target for Rodent family DNA qPCR is the 74 bp Alu-equivalent consensus sequence.

In still another embodiment of the present disclosure, the protein product is selected from group comprising a monoclonal antibody, a therapeutic protein product and a recombinant protein product, or any combination thereof.

In still another embodiment of the present disclosure, the protein product is preferably produced by Chinese Hamster Ovary cell or mouse myeloma cell line-NS0.

In still another embodiment of the present disclosure, the fluorescent reporter is 6-carboxyfluorescein (FAM), and the quencher is Black Hole Quencher 1 (BHQ-1).

In still another embodiment of the present disclosure, the amplified product is detected using assay selected from group comprising SYBR green assay and TAQMAN probe assay.

In still another embodiment of the present disclosure, concentration of the forward and reverse primer is ranging from about 100 to about 800 nM, preferably 400 nM.

In still another embodiment of the present disclosure, the concentration of the probe is ranging from about from about 1000 to about 100 nM, preferably 100 nM.

In still another embodiment of the present disclosure, wherein the annealing is carried out at a temperature 56° C. for time duration of about 1 minute.

In still another embodiment of the present disclosure, minimum amount of the residual genomic DNA in the biological sample detected and optionally quantified is less than about 5 femtograms.

In still another embodiment of the present disclosure, the residual genomic DNA identified from the recombinant protein product comprises of Alu equivalent concensus sequences designated as SEQ ID: 1, SEQ ID: 2, SEQ ID:3, SEQ ID:4, SEQ ID:5, SEQ ID:6 and SEQ ID:9.

In still another embodiment of the present disclosure, the residual genomic DNA using specific Alu equivalent consensus sequences comprises the nucleic acid sequence of FIG. 1.

In still another embodiment of the present disclosure, the primers used in the current disclosure consist of forward and reverse primers.

In still another embodiment of the present disclosure, the forward primer comprises nucleic acid sequence selected from group consisting of SEQ ID NO: 7, SEQ ID NO: 11, SEQ ID No: 14, SEQ ID NO: 19 and SEQ ID NO: 22.

In still another embodiment of the present disclosure, the reverse primers comprises nucleic acid sequence selected from group consisting of SEQ ID NO: 8, SEQ ID NO: 12, SEQ ID No:15, SEQ ID NO: 17, SEQ ID NO: 18, SEQ ID NO: 20 and SEQ ID NO: 23.

In still another embodiment of the present disclosure, the forward and the reverse primers have a sequence as given in SEQ ID NO: 22 and SEQ ID NO: 23.

In still another embodiment of the present disclosure, the single degenerate designed probe comprises nucleic acid sequence selected from group consisting of SEQ ID NO: 10, SEQ ID NO: 13, SEQ ID No: 16, SEQ ID NO: 21, and SEQ ID NO: 24.

In still another embodiment of the present disclosure, the single degenerate designed probe has a sequence set forth in SEQ ID NO: 24.

In still another embodiment of the present disclosure, the primers and the probe are used for detecting and optionally quantifying residual genomic DNA having an Alu sequence, from a biological sample containing a protein product.

In still another embodiment of the present disclosure, the probe comprises a fluorescent reporter 6-carboxyfluorescein (FAM) at 5' end, or a quencher Black Hole Quencher 1 (BHQ-1) at 3' end, or a combination thereof.

The present disclosure further relates to a kit for detecting and optionally quantifying residual genomic DNA having an Alu sequence, from a biological sample containing a protein product, said kit comprising the primer as claimed in claim 18 the probe as claimed in claim 20 and quantitative real-time PCR reagents, optionally along with an instruction manual.

The objective of the disclosure is to design a sensitive method of detecting residual genomic DNA (gDNA) present in a given Biological sample. Such a sensitive method finds application for demonstrating the DNA clearance capacity of the manufacturing process steps (for e.g. affinity chromatography, ion exchange chromatography) that holds the potential to reduce the genomic DNA content present in biological sample to picogram and/or femtogram levels. For example, the concentration of the protein sample provided for DNA estimation from the optimized chromatography stages is typically in range of 5-15 mg/ml. It is assumed that residual DNA quantity in sample from these optimized steps ranges in femtograms (e.g. 50 fg). To facilitate the DNA quantification using a method having sensitivity in picogram levels (for e.g. 1 pg) one has to process high sample volumes during DNA extraction procedure, a limiting factor for both DNA extraction procedure as well as qPCR assays. Other most practical option is to have a method in place with sensitivities in the femtogram range (20 fg as in present disclosure) capable of precise DNA quantification obtained from low sample volumes.

Second application for a sensitive method is when purified biological proteins that are required to be administered at higher dosages. Regulatory agencies expect the DNA levels in such high dosage proteins to be below the specified standards of 10 ng/dose suitable for human use. Having a sensitive method with potential to quantitate DNA as low as 20 fg empowers one to measure and report the precise quantities of residual DNA present in the biological protein thus facilitating compliance for DNA levels. This can be clearly illustrated by an example where therapeutic proteins A, B and C whose single human dosage identified are 300 mg, 1200 mg and 2000 mg respectively. It is assumed that the chromatography process step is optimized and the DNA content in the purified protein is as low as 100 fg/mg. Using methods having sensitivity limits as 1 pg/reaction (method 1, a qPCR based method for residual CHO genomic DNA quantification where the target is other than Alu-equivalent consensus sequence) and 20 fg/reaction (method 2), the DNA levels estimated for a dose would work out as mentioned in Table 1 below:

TABLE 1

Impact of assay sensitivities on DNA quantities estimated for varying doses of therapeutic proteins

| Protein sample | Concentration of Protein sample (mg/ml) | Sample quantity processed (vol) | Protein content analyzed for qPCR reaction | DNA content estimated with Method 1 having sensitivity of 1 pg per reaction | DNA content estimated with Method 2 having sensitivity of 20 fg per reaction | Protein required per human dose | DNA estimated per dose as per Method 1 results | DNA estimated per dose as per Method 2 results |
|---|---|---|---|---|---|---|---|---|
| A | 20 | 200 μl | 0.5 mg | <1 pg | 50 fg | 300 mg | <600 pg | 30 pg |
| B | | | | | | 1200 mg | <2400 pg | 120 pg |
| C | | | | | | 2000 mg | <4000 pg | 200 pg |

The observations from the Table 1 clearly indicate that high sensitivity of the method 2 facilitates precise quantification of the DNA levels per dose of therapeutic protein and provides greater assurance even if high dosage biological proteins are to be analyzed for DNA compliance.

Accordingly, qPCR method is developed using specific primers and probe designed to detect the presence of low concentrations (as low as 20 or 2 femtograms) of residual CHO genomic DNA in the given biological sample.

Another objective of the present disclosure is to determine the presence of residual genomic DNA using specific Alu equivalent consensus sequences as specified in SEQ ID: 1 by using primer sequence ID number 22 and sequence ID number 23 and corresponding probe sequence ID number 24 targeted to amplify Alu family of the dispersed sequences.

Therapeutic recombinant proteins are expressed mainly in CHO cells (Chinese Hamster Ovary cells) and NS0 cells (Mouse Myeloma cell line), belonging to Rodent family. The purified proteins from the bulk harvest is likely to carry traces of host cell genomic DNA into the final formulation thereby posing additional risk. Therefore, regulatory agencies like World Health Organisation (WHO), European Medicine Agency (EMA) or Food and Drug Administration (FDA) have documented in the guidelines the permissible levels of host cell DNA per dose of the drug administered to the patients.

The present disclosure provides a sensitive method for the detection of residual genomic DNA from a mammalian host organism as low as 20 femtogram in a recombinant protein product by using specific primers and probe. The said method comprising of:
  i) Extraction of DNA from the sample
  ii) Designing suitable primers to amplify a region of the CHO genomic DNA and a specific probe designed to anneal to a target sequence located between two PCR amplification primers
  iii) Amplifying the targeted sequences with the pair of specific primers and a DNA-based probe with a fluorescent reporter at one end and a quencher of fluorescence at the opposite end of the probe.
  iv) Breakdown of the probe by the 5' to 3' exonuclease activity of the Taq polymerase which breaks the reporter-quencher proximity and thus allows unquenched emission of fluorescence
  v) The increase in fluorescence and accumulation of the PCR product is continually monitored throughout the PCR reaction by real-time PCR instrument.

Wherein the change of fluorescence in each cycle is proportional to the identification of specific amplified sequences and indicates the presence of residual genomic DNA in the sample.

One embodiment of the present disclosure provides a method of detecting host cell DNA in a given sample using sensitive assay techniques like real time PCR. The method involves extraction of DNA, designing suitable primers to amplify a region of the CHO genomic DNA and monitoring the accumulation of the PCR product with the help of a real time PCR instrument.

Another embodiment of the present disclosure involves detecting and amplifying genomic DNA with the help of specific primers and probes. The probe is designed to anneal to a target sequence located between two PCR amplification primers and is labeled with the fluorescent reporter dye FAM (6-carboxyfluorescein), at the 5' end and the quencher dye, BHQ-1 (Black Hole Quencher 1) at the 3' end. The close proximity of the two dyes leads to the quenching of the reporter dye fluorescence. During polymerization, the exonuclease activity of Taq polymerase cleaves the probe, separating the quencher and reporter dyes, thus resulting in increased reporter dye fluorescence. This increase in fluorescence and accumulation of the PCR product is continually monitored throughout the PCR reaction by real-time PCR instrument. Within the linear range of amplification established for known quantities of DNA, the amount of residual CHO DNA in the sample is extrapolated on standard curve generated from cycle threshold values versus known quantities of CHO genomic DNA.

In one embodiment of the present disclosure, the target for CHO cell DNA qPCR is the Alu-equivalent consensus sequence described by Haynes et al (1981, *Mol. Cell. Biology* 1:573-83).

In another embodiment of the present disclosure, the target sequence is a truncated region of the Haynes sequence as disclosed in SEQ ID NO: 1.

In another embodiment of the present disclosure the primers used in the current disclosure consist of forward and reverse primers.

In another embodiment of the present disclosure the forward and reverse primers used in the current disclosure are disclosed in SEQ ID NO: 22 and SEQ ID NO: 23 respectively.

In another embodiment of the present disclosure the PCR amplified products are detected using SYBR green assay and TAQMAN probe assay.

In still another embodiment of the present disclosure, the Taqman probe disclosed herein has the sequence as seen in SEQ ID NO: 24.

In another embodiment the Taqman probe disclosed in SEQ ID NO: 24 has a single degeneracy which increases the sensitivity and accuracy of the probe as against multiple degenerate bases In yet another embodiment of the present disclosure, the specific sequence of primers and probe disclosed herein, increase the sensitivity and efficiency of the method.

In still another embodiment of the present disclosure, the sequence disclosed in SEQ ID NO: 1 is detected at lower concentrations and much faster when compared to sequences in existing disclosures. As illustrated in example no 4 & 13, the identification of 74 bp sequence as well as the design of primers to amplify the target sequence demonstrates the efficacy of the method.

The term "protein" is meant to include a sequence of amino acids for which the chain length is sufficient to produce the higher levels of secondary and/or tertiary and/or quaternary structure. This is to distinguish from "peptides" or other small molecular weight drugs that do not have such structure. In one embodiment, the proteins used herein have a molecular weight of at least about 47 kD. Examples of proteins encompassed within the definition used herein include therapeutic proteins. A "therapeutically active protein" or "therapeutic protein" refers to a protein which may be used for therapeutic purposes, i.e., for the treatment of a disorder in a subject. It should be noted that while therapeutic proteins may be used for treatment purposes, the disclosure is not limited to such use, as said proteins may also be used for in vitro studies. In a preferred embodiment, the therapeutic protein is a fusion protein or an antibody, or antigen-binding portion thereof. In one embodiment, the methods and compositions of the disclosure comprise at least two distinct proteins, which are defined as two proteins having distinct amino acid sequences. Additional distinct proteins do not include degradation products of a protein.

As used herein the term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparation which typically includes different antibodies directed against different determinants (epitopes), each monoclonal antibody is directed against a single determination on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler et al., Nature 256:495 (1975), or may be made by recombinant DNA methods (see, e.g., U.S. Pat. No. 4,816,567). The "monoclonal antibodies" may also be isolated from phage antibody libraries using the technique described in Clackson et al., Nature 352:624-626 (1991) and Marks et al., J. Mol. Biol. 222:581-597 (1991), for example.

The CHO cells described here may be used as host cells for expression of any protein of interest. This may be done by means known in the art.

Protein expression in CHO cells and cell lines is well described in the literature, and the skilled person will have little difficulty in using the CHO cells and cell lines described here as hosts for protein expression. Thus, for example, the CHO cells and cell lines may be transfected by means known in the art with expression vectors capable of expressing the protein of interest.

As used herein the term "expression" refers to a process by which a polypeptide is produced based on the nucleic acid sequence of a gene. The process includes both transcription and translation.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH).

The term "pharmaceutical formulation" refers to preparations which are in such form as to permit the biological activity of the active ingredients to be unequivocally effective, and which contain no additional components which are toxic to the subjects to which the formulation would be administered.

The phrases "contaminant genomic DNA," "residual genomic DNA," and the like refer to any nucleic acid molecules remaining in the sample, e.g., purified protein sample, pharmaceutical formulation, etc. Nucleic acid molecules remaining in the sample can comprise apoptotic DNA fragments, i.e., fragments of DNA resulting from programmed cell death.

The term "Melting curve analysis" refers to an assessment of the dissociation-characteristics of double-stranded DNA during heating. The information gathered can be used to infer the presence and identity of single-nucleotide polymorphisms, to detect primer dimers, contaminating DNA, and PCR product from mis-annealed primer.

The term Femtogram refers as a unit of mass equal to 0.000 000 000 000 001 grams and with symbol fg. Picogram is a unit of mass equal to one trillionth of a gram ($10^{-12}$), represented as pg.

The term "probe" refers to RNA or DNA fragment, radioactively or chemically labeled, that is used to detect specific nucleic acid sequences by hybridization TaqMan probes depend on the 5'-nuclease activity of the DNA polymerase used for PCR to hydrolyze an oligonucleotide that is hybridized to the target amplicon. TaqMan probes are oligonucleotides that have a fluorescent reporter dye attached to the 5' end and a quencher moiety coupled to the 3' end. These probes are designed to hybridize to an internal region of a PCR product. In the unhybridized state, the proximity of the fluorophore and the quench molecules prevents the detection of fluorescent signal from the probe. During PCR, when the polymerase replicates a template on which a TaqMan probe is bound, the 5'-nuclease activity of the polymerase cleaves the probe. This decouples the fluorophore and quenching dyes and FRET no longer occurs. Thus, fluorescence increases in each cycle, proportional to the amount of probe cleavage.

As used herein the term Quenching refers to any process which decreases the fluorescence intensity of a given substance.

As used herein the term Taqman degenerate probe is also called as double labeled oligonucleotides or double dye probe where one of the nucleotide is a degenerate base such as R=A or G nucleotide. A fluorophore is attached to the 5' end of the probe and a quencher to the 3' end. The fluorophore, FAM (6-carboxyfluorescein) is excited by the machine and passes its energy to the quencher, black hole quencher (BHQ).

As used herein the term 5'-3' exonuclease activity of the thermostable enzyme *Thermus aquaticus* DNA polymerase may be employed in a polymerase chain reaction product detection system to generate a specific detectable signal concomitantly with amplification.

The Ct (cycle threshold or cycle number) is defined as the number of cycles required for the fluorescent signal to cross the threshold (i.e. exceeds background level). Ct levels are inversely proportional to the amount of target nucleic acid in the sample (i.e. the lower the Ct level the greater the amount of target nucleic acid in the sample).

As used herein the term SYBR Green refers to a highly specific dye that binds to minor grooves of the double stranded DNA to detect the PCR product as it accumulates during the qPCR reaction. SYBR green assay provides the simplest and most economical format for detecting and quantitating PCR products in real-time reactions. SYBR Green upon excitation emits light. Thus, as a PCR product accumulates, fluorescence increases. The advantages of SYBR Green are that it is inexpensive, easy to use, and sensitive.

The disclosure is further elaborated with the help of following examples. However, these examples should not be construed to limit the scope of the disclosure.

EXAMPLES

Example: 1

Biological Sample:
Any monoclonal antibodies or therapeutic proteins expressed in CHO—S cell line (obtained from Invitrogen cat#11619012).
Preparation of Standard DNA:
Genomic DNA from CHO cells is extracted from monoclonal antibody production strain by following phenol chloroform extraction method. DNA is resuspended in 10 mM Tris-1 mM EDTA, pH 8.0, the concentration determined, and diluted to a storage concentration of 100 ng/µL and a working concentration of 10 ng/µL. This DNA is used as Standard in qPCR.

Extraction of DNA from Biological Sample:

DNA from biological sample is extracted by using silica based DNA extraction columns where DNA binds to the silica membrane due to change in pH to acidic and DNA is eluted from the membrane with the addition of water which changes pH to neutral.

Example: 2

Materials and Method

The primers are obtained from Eurofins (Germany) and probe from Eurogentec (Belgium). Real time PCR machines Mx3000P from Stratagene and Realplex$^2$ from Eppendorf is used in this study. Reagents for Taqman qPCR are obtained from Thermo-Absolute qPCR probe master mix. SYBR green master mix is obtained from Bioline.

Example: 3

Determination of Alu-Equivalent Consensus Sequence:

The target for CHO cell DNA qPCR is the Alu-equivalent consensus sequence described by Haynes et al., Based on the 74 bp consensus sequences, forward and reverse primers are designed and used for qPCR. The template DNA for qPCR is extracted from the CHO cells routinely used for expression of biotherapeutic proteins. Six PCR reactions from different concentration of CHO genomic DNA starting from 2 ng are performed to confirm the presence of single band with the expected size of 74 bp. Reconfirmation is done using automated capillary based gel electrophoresis-Multi NA (Schimadzu). Each PCR product is subcloned into high copy number E. coli vector using blunt end cloning kit (Fermentas), transformed into chemically competent E. coli cells and plated on selection plates. From each transformation, 10 colonies are randomly selected (60 transformants) and screened for the presence of the insert by PCR.

95% of the transformants are positive for the presence of insert and among them 5 positive clones are selected for plasmid isolation and sequencing. The sequence of 5 clones is aligned using CLUSTAL W online software. An alignment of the six sequences including the consensus sequence is shown in FIG. 1.

Example: 4

Primer and Probe Optimization:

Primers are designed to amplify a region of CHO Genomic DNA, and a specific probe designed to anneal to a target sequence located between two PCR amplification primers is labeled with the fluorescent reporter dye, FAM (6-carboxyflourescein), at the 5' end and the quencher dye, BHQ-1 (Black Hole Quencher 1), at the 3' end. The close proximity of the two dyes leads to quenching of the reporter dye fluorescence. During polymerization, the exonuclease activity of Taq polymerase cleaves the probe, separating the quencher and reporter dyes, thus resulting in increased reporter dye fluorescence. This increase in fluorescence and accumulation of the PCR product is continually monitored throughout the PCR reaction by real-time PCR instrument. Within the linear range of amplification established for known quantities of DNA, the amount of residual CHO DNA in the sample is calculated by extrapolating on standard curve generated from cycle threshold values versus known quantities of CHO genomic DNA.

The development of residual DNA detection assay started with the novel designing of primers based on the Haynes Sequence (Mol. Cell. Biology 1:573-83). Seq ID nos 7 and 8 represent the forward qPCR primer and reverse qPCR primer respectively. Using these qPCR primers, SYBR green assay is performed where the concentration of the primers used is 100 nM. See FIG. 2a for the amplification plots obtained.

To improve the melting curve (FIG. 2b) for obtaining tapering and sharp peaks, the annealing temperature and concentration of forward and reverse primers are optimized.

To optimize the annealing temperature, a gradient qPCR is performed in the temperature range of 55° C. to 65° C. in Realplex$^2$ qPCR machine from Eppendorf where the primer concentration is maintained at 100 nM. The melt curve analysis revealed that 64° C. annealing temperature is optimal as at this temperature the melting curve showed a peak comparatively better than those observed at other temperatures within the temperature range (see FIG. 3). All the subsequent experiments are further carried out at 64° C. as annealing temperature.

To further improve the appearance of the melting curve or to specifically amplify the specific target, the primer concentration is varied. The concentration of forward and reverse primers is optimized to achieve early $C_T$ in amplification plot graph with a PCR product showing a single peak in a melting curve analysis in the SYBR green qPCR.

Both the primers are titrated at 100 nM, 200 nM, 400 nM and 800 nM concentrations and the $C_T$ values are subsequently compared. During these primer optimization trials, a single concentration of CHO genomic DNA (2 ng) is used. At 400 nM concentration both forward and reverse primers gave higher fluorescence and $C_T$ (Cycle threshold) at ~15, and is used in subsequent experimentation where the primer efficiency is checked across DNA dilution range (FIGS. 4a and 4b).

The PCR product is sequenced by cloning the fragment into E. coli high copy number vector and transformed into the E. coli competent cells. The transformants are screened for the presence of the insert. Seq ID no 9 represents the sequence of the target obtained from the positive clone plasmid (FIG. 5).

Based on these results, a probe is designed to perform Taqman assay for specific amplification of the DNA where the probe binds to the target and emits fluorescence.

A Taqman qPCR assay is performed using the qPCR Probe SEQ ID no. 10 and primers forward and reverse SEQ ID no 7 and 8 with the CHO genomic DNA. The concentration of the probe used is 20 nM. The assay results revealed that the amplification plots are not sigmoid; instead drooping plots are obtained (FIG. 6a) indicating inefficient reaction between primer, probe and template DNA.

Further, to improve the appearance of the amplification plots, the probe concentration is titrated against varied primer concentrations at 64° C. as annealing temperature. No improvement is observed in the appearance of the amplification plots as observed in the FIG. 6a.

Gradient PCR with temperature ranging from 53° C. to 63° C. is performed where the forward and reverse primer concentration of 400 nM and probe of 20 nM is used. 55° C. temperature showed the plots with highest fluorescence intensity, however the $C_T$ obtained is at cycle number ~18 indicating delayed amplification of target DNA.

Hence the primers and the probe are redesigned based on the sequence of the specific target. SEQ ID NOs: 11 and 12 correspond to the redesigned primers as shown in the highlighted region on SEQ ID NO: 9. The difference in redesign of forward primer is deletion of 2 bases at the 5' end and addition of 3 bases at the 3' end as compared to SEQ ID NO: 7. Similarly for the redesign of the reverse primer (SEQ ID NO: 12), 3 bases are deleted at the 3' end as compared to the SEQ ID NO: 8. The redesigned reverse primer is depicted by highlighted region on the complementary strand of the SEQ ID NO: 9 (FIG. 6b). The amplicon length using SEQ ID NOs: 11 and 12 primers are found to be 69 bp.

Taqman qPCR assay is performed using 400 nM concentration of the redesigned primers seq ID no 11 and 12 and 20 nM concentration of the Taqman qPCR probe Seq ID no 10. Three standard DNA dilutions-2 ng, 200 pg and 20 pg are used to perform the assay. The probe/primers binding efficiency to the template DNA is found to be inappropriate as shown by wavy amplification plots (FIG. 7).

Based on these results, another probe is designed to bind to the target more efficiently resulting in better appearance of the amplification plots. Seq ID no 13 represents the sequence of the Taqman qPCR probe.

On using Taqman probe (seq ID 13) with seq ID nos 11 and 12 primers on the template DNA, it is found that no amplification plots are observed indicating the poor performance of the probe as well as primers. The efficiency of the probe binding to the target is not good and hence the primers and probe are redesigned.

Seq ID nos 14 and 15 represent the sequence of the new forward and reverse primers and SEQ ID no 16 represents the sequence of the new Taqman probe.

The designing strategy is changed where the forward primer is designed on the complementary strand of SEQ ID NO: 9 (shown by highlighted region in FIG. 8a) and similarly the reverse primer is designed on the sense strand (shown by highlighted region in FIG. 8a) on SEQ ID NO: 9. The amplicon length is reduced to 66 bp with this design. The probe region (SEQ ID NO: 16) in the SEQ ID NO: 9 is shown in underlined font in FIG. 8a.

When the Taqman qPCR assay is performed using the forward and reverse primer SEQ ID nos 14 and 15 along with Taqman qPCR probe SEQ ID 16, the amplification of the standard DNA dilutions is not observed (FIG. 8b). The reason could be the inefficient binding of primers and/or probe with the target DNA.

After unsuccessful attempts of designing of optimum primer and probe combinations within 71 bp Alu-equivalent sequence, we explored sequence length flanking the 3' end of the SEQ ID 9. It is observed that the sequences downstream of 3' end of 71 bases are falling in 2 lineages. One of the lineages had sequence stretch of ~293 bases designated as lineage 1 and another lineage (lineage 2) is having a sequence stretch of 420 bases. The reverse primers are designed from both the lineages using online available software (PrimerQuest from Integrated DNA technologies). The best primer design results from the software for lineage 1 had amplicon length of 180 bases where as for lineage 2 it is 355 bases. The sequence stretches from lineage 1 and 2 are shown in FIG. 9 and FIG. 10. Using forward primer seq ID no 7 and reverse primer seq ID no 17 from lineage 1, SYBR green qPCR assay is performed at 60° C. annealing temperature. Delayed amplification plot for the standard DNA is observed at cycle number 25 and a blunt melting curve is observed for the standard DNA dilution.

Similar results are observed for qPCR results using forward primer SEQ ID 7 and reverse primer SEQ ID 18 from lineage 2. Amplification plot for standard DNA is observed at cycle number 32 and a sharp melting curve. The delayed cycle number made this primer inefficient (FIG. 11).

These results indicate that the sequence stretch beyond 71 bases (like sequence stretch of 293 and 420 bases) are inefficient in providing targets for the residual DNA estimation assay as the DNA amplification is observed in the later cycles (beyond 25 cycles) and hence are not suitable. Therefore it is apparent that one should confine and optimize the target in and around the identified 71 base region in Alu-equivalent sequence.

Based on the above observations from the experiments, redesigning of primers is initiated considering and confining the design around 71 bp Alu equivalent sequence target. The forward primer SEQ ID no 19 is designed with the addition of 2 bases at the 5' end and deletion of 1 base at the 3' end of the seq ID no 7 forward primer. Similarly the reverse primer SEQ ID no 20 is designed with the addition of 5 bases at the 5' end and deletion of 3 bases at the 3' end of the seq ID no 8 reverse primer. The amplicon size is found to be 79 bp (FIG. 12).

Upon performing SYBR green assay using the SEQ ID 19 and 20 primers with the CHO DNA, good amplification plots and sharp melt curve is obtained indicating the amplification of specific target (FIGS. 13a and 13b).

Several PCR reaction are set using the qPCR primer SEQ ID nos 19 and 20 and different concentrations of standard CHO genomic DNA. The PCR amplified products from downstream processing samples are sequenced and aligned using the online software-CLUSTAL W. The variance of Alu-equivalent sequences are observed on sequencing and aligning the PCR products (FIG. 14).

Based on the variations observed in the alignment (FIG. 14), a degenerate probe is designed. The aim of designing a degenerate probe is to attain broad dynamic range so as to have reactivity with the sequence variants identified during alignment as well as provide high sensitivity and differential signal to background ratio. Seq ID no 21 represents the degenerate Taqman qPCR probe.

Degenerate qPCR probe seq ID no 21 along with the forward and reverse primer SEQ ID 19 and 20 is used to set up a Taqman qPCR. Standard DNA dilutions of 2 ng, 200 pg and 20 pg are analyzed in Mx3000P Stratagene machine. Inefficient amplification plots are obtained that is wavy instead of being sigmoidal (FIG. 15).

Taking a clue from the inefficient binding of designed primer/probe, further modifications are made. To the existing forward primer SEQ ID no 19, 2 bases are added at the 3' end to modify the primer as represented by SEQ ID no 22. The reverse primer is also modified by addition of 3 bases at the 3' end and deletion of 5 bases at the 5' end. SEQ ID no 23 represents the reverse primer after modification. The amplicon length is found to be 74 bp (FIG. 16).

A novel degenerate probe with only 1 degenerate base is designed (represented by seq ID no 24) in order to reduce the degeneracy in the probe which might have an impact on the efficiency and probe binding to the target.

Using the primer SEQ ID 22 and 23 and probe seq ID no 24 Taqman assay is performed at 56° C. annealing temperature. The CHO standard DNA dilutions from 2 ng to 20 fg are analysed and the amplification signals are detected as early as ~15 cycle number indicating that the binding efficiency of primer and probe are compatible with the template DNA (see FIG. 17).

Both the primers are titrated at 100 nM, 200 nM, 400 nM and 800 nM concentrations in the SYBR green assay. During these primer optimization trials, a single concentration of CHO genomic DNA is used. At 400 nM concentration both forward and reverse primers gave higher fluorescence and early $C_T$ at cycle no. ~12 is seen. The 400 nM concentration of forward and reverse primer (SEQ ID 22 and 23) is used in subsequent experimentation (See FIGS. 18a and 18b).

Degenerate qPCR probe SEQ ID 24 along with the forward and reverse primer SEQ ID no 22 and 23 is used to set up a Taqman qPCR. Standard DNA dilutions of 2 ng, 200 pg, 20 pg, 2 pg, 0.2 pg and 20 fg are analysed in Realplex² (Eppendorf) machine (see FIG. 19). The DNA amplification is observed from cycle ~15 and is uniform across all the standard dilutions. The reaction had annealing temp of 56° C.

After primer concentration, Taqman probe concentration is titrated at 1000 nM, 500 nM, 400 nM, 200 nm and 100 nM concentrations and the $C_T$ values are subsequently compared. Significant improvements in the appearance of the amplification plots and sensitivity are noted with change in probe concentration. Concentration of probe is optimized to 100 nM based on the appearance of the amplification plots and early $C_T$ values and this is the concentration used for subsequent experimentation (see FIG. 20).

Based on the above experiments, the forward/reverse primer and probe design is finalized for assay development activity. The forward and reverse primers (SEQ ID 22 and 23) are designated as "forward qPCR primer" and "reverse qPCR primer" respectively. Similarly probe with SEQ ID 24 is designated as "Degenerate qPCR Probe".

Example: 5

Annealing Temperature Optimization

Annealing temperature optimization is done to get early $C_T$, sigmoid amplification plots and a single peak in melting curve in SYBR green qPCR. Using gradient PCR (Realplex2), between 50° to 60° C., the annealing temperature is optimized to 56° C., at which the melting curve showed a single neat peak signifying amplification of a single product. At the same temperature the probe based Taqman qPCR is also optimized and is used for subsequent experimentation.

Example: 6

DNA preparation using QIAamp Viral RNA Kit

The extraction protocol is optimized to improve the recovery of residual genomic DNA from the samples received from the therapeutic proteins purification process. 200 µl of the sample spiked with genomic DNA (positive control) is treated with 560 µl Buffer AVL-lysis buffer in the presence of carrier RNA. This is allowed to react for 5 mins at room temperature. To this, 560 µl of absolute alcohol is added and mixed by pipetting. 640 µl of the mixture is loaded onto the column provided in the kit and centrifuged at 4500 rpm for 2 mins. Flow through is discarded and remaining mixture is loaded again and centrifuged at 4500 rpm for 2 mins. After discarding the flow through the empty column is centrifuged at 8000 rpm for 2 mins. 500 µl of wash buffer AW1 is added and centrifuged at 8000 rpm for 2 mins followed by 2 mins centrifugation at 12000 rpm. Flow through is discarded and 500 µl of wash buffer AW2 is added with changing the collection tube and centrifuged at 12000 rpm. Flow through is discarded, followed by dry spin for 2 mins at 13000 rpm. To elute the bound DNA, 40 µl of water preheated to 70° C. is added, incubated at 70° C. for 20 mins and centrifuged at 12000 rpm for 2 mins. The elution step is repeated to get a final elution volume of 80 µl. Similar protocol is followed for a test sample without spike DNA which serves as unspiked sample.

Example: 7 qPCR Reaction.

The qPCR reaction is set up in a dedicated PCR preparation room to avoid contamination related issues.

The cocktail preparation, addition of extracted test sample to PCR tubes and standard DNA dilution (and addition) is performed in dedicated rooms. All the samples and standards are analyzed in triplicates. Each 50 µl reaction consisted of PCR grade water-4 µl (in case of SYBR green assay) or 3 µl (in case of Taqman assay), 1× master mix-25 µl [Sensimix SYBR green (cat no QT625-05) or Absolute Taqman qPCR (cat no AB-1136/A) master mix-composition not disclosed by the manufacturer], 400 nM of each forward and reverse primer and 100 nM of probe is used whenever Taqman qPCR assay is performed. The template DNA added to the standard DNA dilution tubes is 20 µl. In case of No template control, water is added instead of template DNA. Rest of the tubes are then moved to the dedicated sample preparation room. For spike and/or unspike samples, 10 µl of PCR grade water and 10 µl of extracted DNA from samples is added. The strips are sealed and centrifuged briefly. It is run on Stratagene Mx3000P instrument using the standard thermal cycler protocol which consisted of
1) Initial denaturation or Polymerase activation step at 95° C. for 15 mins (Absolute Taqman qPCR master mix) or 10 mins (Sensimix SYBR green master mix).
2) 40 cycles of denaturing at 95° C. for 15 seconds and annealing/extension at 56° C. for 1 min.

Example: 8

Standard Curve Preparation.

The stock CHO genomic DNA used for standard DNA dilutions is extracted and prepared from the CHO cells that are used for the production of biotherapeutic proteins. The extracted DNA is quantitated using Nanodrop spectrophotometer (Thermo scientific). The purity of DNA is assigned using absorbance ratio at 260/280 nm. The purity as depicted from the ratio is found to be in the range of 1.8 to 2.0 (Molecular cloning, a laboratory manual by Sambrook & Russel, Third edition, Cold Spring Harbor laboratory press).

The starting stock of DNA is maintained at 100 ng/µl. Ten fold serial dilutions of the stock DNA is performed to obtain standards of 10 ng, 100 pg, 10 pg, 1 pg, 100 fg, 10 fg and 1 fg. These standard dilutions are used to achieve standard curve of 2 ng, 200 pg, 20 pg, 2 pg, 200 fg and 20 fg in qPCR.

Example: 9

Specificity of the Assay

To check the specificity and reactivity of the primers and probe, genomic DNA from different sources are used as template. DNA from mammalian sources (other than CHO) like NS0 and human, non-mammalian sources (*E. coli* and *Pichia*) are used. The results showed that the primers are reacting only to CHO and NS0 as NS0 also belongs to rodent family and it is well known in literature that the Alu-equivalent sequences are dispersed across rodent family. Other sources of DNA like human, *E. coli* and *Pichia* did not show reactivity to primers and probe, establishing the specificity of the primers.

Based on the primer reactivity result to NS0 template DNA the qPCR primers seq ID nos 22 and 23 and degenerate probe seq ID no 24 are used to identify the presence of Alu equivalent sequences in NS0 cell line also. The optimized concentrations of primers and probe are used for the DNA concentrations 2000 pg, 200 pg, 20 pg, 2 pg and 0.2 pg. Results are shown in the Table no. 2.

TABLE 2

Comparison of $C_T$s of standard DNA dilutions of CHO and NS0 gDNA using SEQ ID nos 22 and 23.

| Amount of Standard DNA (pg) | $C_T$s with CHO gDNA | $C_T$s with NS0 gDNA |
|---|---|---|
| 2000 | 15.85 | 23.89 |
| 200 | 19.50 | 27.27 |
| 20 | 23.04 | 30.81 |
| 2 | 26.60 | 34.34 |
| 0.2 | 30.38 | 38.13 |

The results revealed that the primers react with NS0 genomic DNA also, confirming the presence of Alu Equivalent sequences in NS0 cell lines.

Host cell DNA estimation in therapeutic proteins expressed from NS0 cell line is done according to the Example 6. The experiment is set up to evaluate the NS0 gDNA detection capability of the forward and reverse primers along with degenerate probe. The standard curve preparation and setting up qPCR reaction is exactly followed as described in Examples 7 and 8.

On analysis of samples, the assay is able to detect as little as 0.3 pg of residual NS0 gDNA in the therapeutic protein expressed in NS0 cell line (Table 3).

TABLE 3

Detection capability of primers Seq ID 22 & 23 and probe seq ID 24 with NS0 cell line derived biological sample.

| Amount of Standard DNA (pg) | $C_T$s with NS0 gDNA | Mean DNA quantity |
|---|---|---|
| 2000 | 23.73 | NA |
| 200 | 27.61 | NA |
| 20 | 31.03 | NA |
| 2 | 33.38 | NA |
| 1 | 34.98 | NA |
| Biological sample | 36.57 | 0.3 pg |

The PCR amplified NS0 gDNA product is cloned into *E. coli* high copy number plasmid and the sequence of the insert is verified and compared with the SEQ ID 1 (CHO gDNA). Nucleotide sequence revealed degeneracy in the probe binding region in NS0 gDNA as compared to CHO gDNA (SEQ ID 1) as shown in FIG. 25.

Example 10

Sequence Comparison of the Target Sequence with Other Alu Targets.

The target sequence designated as SEQ 1 is compared with the Alu-equivalent sequences available in public domain. Since the rational of seq ID 27 & Seq ID 28 is being used as target Alu sequence for residual DNA quantification from biological proteins as described in patents US2009325175 and U.S. Pat. No. 5,393,657 respectively. Therefore the following sequence comparison of Seq ID 1 with Seq ID 27 & 28 was performed to identify the sequence variations between the target identified in present disclosure and those reported in public domain.

The published sequences designated as SEQ ID 27 and SEQ ID 28 are compared with the seq ID 1 using the CLUSTAL W online software. The percentage homology observed with the sequence ID 27 is 50% and hence the percentage variance is 50% (FIG. 21a). The comparison of sequence ID 1 with the sequence 28 revealed percent homology as 71.6% and hence the percent variance is 28.4% (FIG. 21b). These comparisons revealed the persisting difference in sequence between SEQ ID 1 and other published Alu target sequences.

Example 11

Presence of Other Alu Targets in the Genomic DNA.

The two PCR products amplified from CHO genomic DNA by using the primers SEQ ID 25 and SEQ 26 and SEQ ID 29 and SEQ ID 30 are sequenced. Sequencing results revealed the presence of similar sequences with 5% variation with that of the SEQ ID 27 (FIG. 22a) and 21% variance with that of the SEQ ID 28 (FIG. 22b).

Example 12

Comparison of Primer Characteristics:

The important parameters to be considered when selecting or designing PCR primers are the ability of the primer to form a stable duplex with the specific site on the target DNA, and no duplex formation with another primer molecule or no hybridization at any other target site. The primer stability can be measured in the length (base pairs), hairpin loop and dimer formation, the % GC, kcal/mol (duplex formation free energy, $\Delta G$) or in melting temperature. The qPCR primers seq ID nos 22 and 23 are compared with the other primers SEQ ID 25 and 26. See Table 4.

TABLE 4

Represents the comparison of primers parameters.

| Parameters | Seq ID no 22 | Seq ID no 23 | Seq ID no 25 | Seq ID no 26 |
|---|---|---|---|---|
| Length | 24 | 22 | 22 | 23 |
| Molecular weight | 7559.9 | 6883.5 | 6767.4 | 7110.7 |
| % GC | 54.2 | 50 | 45.5 | 52.2 |
| Tm | 59.7 | 55 | 54.0 | 55.3 |
| % GC Tm | 54 | 49.7 | 47.9 | 51.9 |
| $\Delta G$ | −40.4 | −34.6 | −34.4 | −34.5 |
| 3' End $\Delta G$ | 6.1 | 6.4 | 6 | 6.4 |
| Dimers | 6 | 3 | 7 | 10 |
| Hairpin loops | 2 | 1 | 2 | 4 |

On analyzing the primer parameters, it is found that the SEQ ID 22 has higher molecular weight, % GC, Tm and larger negative value for $\Delta G$. It is known from publications that larger negative value for $\Delta G$ indicates stable, undesirable structures of the primers which helps in efficient binding to the target. The possibility of dimer and hairpin loop formation for SEQ ID 23 is lesser than SEQ ID 22, 25 and 26. Higher dimer formation results in inefficient primer binding to the template and hence reduces the product yield. Hairpin loop formation at its 3' end is troublesome, since this can cause internal primer extension, thus eliminating a given primer from the reaction. Hairpins near the 5' end, however, do not significantly affect the PCR.

The % GC of the SEQ ID no 1 is 55.4% and the % GC of the other target SEQ ID 27 is 57.6%. According to the published data, typically, primers should have a % GC similar to or higher than that of the amplified template. In this case, the % GC of the seq ID no 22 is close to its respective target (i.e. SEQ ID 1) while in case of SEQ ID no 25 having % GC 45.5 is lesser than its respective target which is 57.6%.

As illustrated in example 13 and table 5, the use of primer sequences Seq ID no 22 & 23 for qPCR method facilitates early amplification by ~3 cycles for all standard DNA dilution points with respect to the use of primer seq IDs 25 & Seq ID 26 for same quantity of template DNA. The early amplification is due to the cumulative effect of lower dimer & hairpin loop characteristics of Seq ID 22 & Seq ID 23 primer combination used for the method (Table 4). As a result, the self reactivity of the primers is low & affinity towards the template DNA is enhanced leading to optimum qPCR reaction results (Selection of primers for Polymerase Chain reaction". Methods in Molecuar Biology, Vol 15, Humana Press Inc).

Based on these results and observations, primer pairs i.e., SEQ ID 22 and 23 used in present disclosure are better in most of the essential parameters discussed above than the SEQ ID 25 and 26.

Example 13

SYBR Green qPCR:

qPCR SYBR green assay is performed with the primers SEQ ID 25 and SEQ ID 26 with the CHO genomic DNA as template. The standard DNA dilutions used are 2 ng, 200 pg, 20 pg, 2 pg and 1 pg. The first standard DNA dilution amplified at cycle number 15.61 (Table 5). On analysis of melting curve, it is observed that there exists high proportion of degeneracy in Alu equivalent target sequences for the compared primers SEQ ID 25 and 26. This is reflected by the irregular pattern of the melt curves for the standard DNA dilutions used in the assay (FIG. 23a).

Similarly qPCR SYBR green assay is performed with the primers SEQ ID 29 and 30 with the present disclosure CHO genomic DNA as template. The standard DNA dilutions used are 2 ng, 200 pg, 20 pg, 2 pg, and 1 pg. The first standard DNA dilution amplified at cycle number 15.39 (Table 5). On analysis of melting curve, it is observed that there exists high proportion of degeneracy in Alu equivalent target sequences designated as SEQ ID 28. This is reflected by the irregular pattern of the melt curves for the standard DNA dilutions used in the assay (FIG. 23b).

Similar analysis of the primers SEQ ID 22 and SEQ ID 23 with the CHO genomic DNA is performed in SYBR green assay.

At similar dilution pattern starting with 2 ng to 20 fg, the first DNA dilution amplified at cycle number 12.47 which is ~3 cycles earlier than the amplification observed with either SEQ ID 25 and 26 or SEQ 29 and SEQ 30 (Table 5). This clearly establishes that the target existing in the genomic DNA is in higher proportion. The reactivity or efficiency of the primers SEQ ID 22 and 23 and the template ID 1 is comparatively higher with respect to the primers from published data.

In addition, the melt curve analysis depicted that the extent of degeneracy in the target sequence is comparatively less than those existing in targets amplified using primers SEQ ID 25 and 26 and SEQ ID 29 and SEQ ID 30. This is indicated by a single narrow peak of melt curve obtained from all the standard DNA dilutions used in the assay (as shown in FIG. 23c).

TABLE 5

Represents the comparison of cycle numbers of amplification of each dilution of standard DNA in standard curve with SEQ ID no 22 and 23 and other primers

| Conc. of Std. DNA | Primers $C_T$ (SEQ ID 22 and SEQ ID 23) | Primers $C_T$ (SEQ ID 25 and 26) | Primer $C_T$ (SEQ ID 29 and SEQ ID 30) |
|---|---|---|---|
| 2000 pg | 12.47 | 15.61 | 15.39 |
| 200 pg | 15.54 | 19.26 | 18.82 |
| 20 pg | 19.26 | 23.18 | 22.07 |
| 2 pg | 23.22 | 26.66 | 26.20 |
| 0.2 pg | 26.71 | 30.45 | 30.30 |
| 0.02 pg | 30.14 | 34.27 | 33.68 |

Example 14

Taqman Probe qPCR Assay:

Taqman probe assay is more specific compared to SYBR green as probe detects the target specifically on reacting to the complementary template strand.

Taqman probe with single degenerate base is designed for the SEQ ID 1.

The DNA dilutions are performed similar to the one mentioned in example number 7. The thermal cycling conditions have been defined in the example number 6. The concentration of the probe added to the qPCR cocktail is optimized to 100 nM and primer concentration used is 400 nM Forward and Reverse primer (SEQ ID 22 and 23 respectively) per reaction. The first DNA dilution (2 ng) in the standard curve amplifies at ~15 cycle number and the last DNA dilution (20 fg) of the standard curve amplifies at cycle number 32 (see FIG. 24a and Table 6). The PCR efficiency is found to be 100.8% with correlation coefficient ($R^2$) for reaction being 1. Slope of the standard curve is –3.3 (FIG. 24 b).

TABLE 6

Represents the cycle numbers of amplification of each dilution of standard DNA in standard curve obtained by using the primers SEQ ID no 22 and SEQ ID 23 with its respective Taqman probe SEQ ID 24.

| Conc of Std DNA | $C_T$ (Seq ID 22 and Seq Id 23) |
|---|---|
| 2000 pg | 15.95 |
| 200 pg | 19.37 |
| 20 pg | 22.55 |
| 2 pg | 25.84 |
| 0.2 pg | 29.3 |
| 0.02 pg | 32.53 |

To evaluate the performance of the Taqman assay, different downstream purification stage samples (200 μl) were analysed for the detection of the host cell DNA. Table 7 represents the Ct values & mean quantities of standard DNA dilutions along with the biological samples (CHT4 US, 098US, C1089US, C1098US & C2089 US). The PCR efficiency was found to be 0.9 with a slope of –3.57 & $R^2$ being 1.

TABLE 7

Represents the Ct values & mean quantities of standard DNA dilutions with the analysed biological samples.

| Sample Description | $C_t$ Value | Mean Quantity |
|---|---|---|
| Standard 1 | 16.4 | 2000 pg |
| Standard 2 | 19.85 | 200 pg |
| Standard 3 | 23.6 | 20 pg |

TABLE 7-continued

Represents the Ct values & mean quantities of standard
DNA dilutions with the analysed biological samples.

| Sample Description | $C_t$ Value | Mean Quantity |
|---|---|---|
| Standard 4 | 27.1 | 2 pg |
| Standard 5 | 30.65 | 200 fg |
| Standard 6 | 34.21 | 20 fg |
| CHT4 US | 35.38 | 15 fg |
| 098 US | 37.52 | 2.4 fg |
| C1089 US | 36.79 | 3.8 fg |
| C1098 US | 39.49 | 7.07 fg |
| C2089 US | 36.1 | 6.3 fg |

Example 15

CHO Residual DNA Quantification Kit:

The developed method can be used as a kit to detect the residual CHO DNA in the biotherapeutic/biopharmaceutical products. Using the Taqman technology, the limitations of the traditional methods can be overcome by enabling rapid, specific quantification of femtogram levels of CHO host cell DNA. Reliable assay performance and quantitative results can be obtained in two hours, allowing high-confidence for testing across broad range of sample types, from in-process samples to final drug substance for lot release. Components of the Taqman residual DNA kit comprises of:

Forward primer.
Reverse primer.
Taqman Probe.

The DNA to be estimated is extracted from the therapeutic proteins to overcome the interference caused by the proteins present using commercial extraction kit. The purified DNA is then analysed in the presence of the Taqman master mix, primers and probe.

Taqman master mix such as Absolute qPCR probe master mix from Abgenes, UNG Taqman master mix from Eurogentec and Platinum® Quantitative PCR SuperMix-UDG from Invitrogen can be used.

The Taqman CHO residual DNA detection kit provides a highly sensitive detection of CHO DNA, allowing the use of small sample volumes to generate accurate results. The broad linear range provided by Taqman technology allows testing of samples containing variable levels of CHO DNA, such as, as high as nanogram levels in in-process samples to as low as femtogram levels in drug substance. FIGS. 26 and 27 demonstrates the range and sensitivity of the assay.

We claim:

1. A sensitive and quantitative method to detect residual genomic DNA from a host cell of rodent family as low as 2 femtogram in a protein product by using primers consisting of SEQ ID NO: 22 and SEQ ID NO: 23 and corresponding probe consisting of SEQ ID NO: 24 targeted to amplify Alu family of the dispersed sequences, wherein host cell is a CHO or NS0 cell, comprising the steps of:
   a. providing DNA extracted from the sample;
   b. amplifying the targeted Alu sequences with the pair of primers using quantitative real time PCR (qPCR) and annealing said probe to said target sequences, wherein the probe comprises a fluorescent reporter at one end and a quencher of fluorescence at the opposite end of the probe;
   c. breakdown of the probe by 5' to 3' exonuclease activity of Taq polymerase so as to break the reporter-quencher proximity and allow unquenched emission of fluorescence; and
   d. continually monitor the increase in fluorescence and accumulation of the PCR product throughout the PCR reaction by real-time PCR
   wherein the change of fluorescence in each cycle is proportional to the identification of specific amplified sequences and indicates the presence of residual genomic DNA in the sample.

2. The method as claimed in claim 1, wherein the target for CHO genomic DNA qPCR is a sequence as set forth in any of SEQ ID NOs: 2 to 6 and SEQ ID NO: 9.

3. The method as claimed in claim 1, wherein the protein product is selected from group comprising a monoclonal antibody, a therapeutic protein product and a recombinant protein product, or any combination thereof.

4. The method as claimed in claim 1, wherein the protein product is produced by Chinese Hamster Ovary cell or mouse myeloma cell line-NS0.

5. The method as claimed in claim 1 wherein the fluorescent reporter is 6-carboxyfluorescein (FAM), and the quencher is BHQ

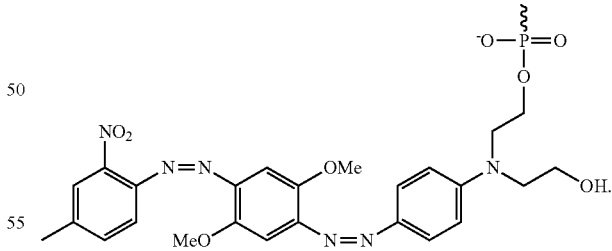

6. The method as claimed in claim 1, wherein concentration of the forward and reverse primer is ranging from about 100 to about 800 nM each.

7. The method as claimed in claim 1, wherein the concentration of the probe is ranging from about from about 1000 to about 100 nM.

8. The method as claimed in claim 1, wherein the annealing is carried out at a temperature 56° C. for time duration of about 1 minute.

9. The method as claimed in claim 1, wherein the probe comprises a fluorescent reporter 6-carboxyfluorescein (FAM) at 5' end, or quencher

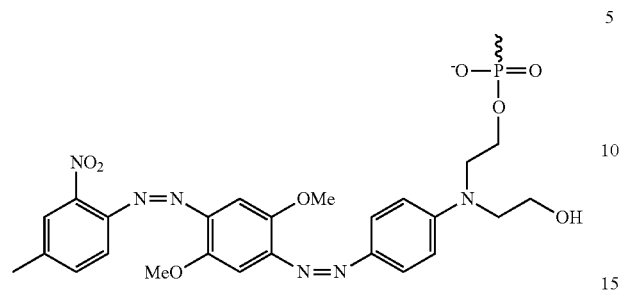

at 3' end, or a combination thereof.

10. A kit for detecting and optionally quantifying residual genomic DNA having an Alu sequence from a CHO or NS0 cell as low as 2 femtogram in a protein product, said kit comprising primers consisting of SEQ ID NO: 22 and SEQ ID NO: 23 and corresponding probe consisting of SEQ ID NO: 24, wherein the probe comprises a fluorescent reporter at one end and a quencher of fluorescence at the opposite end of the probe and quantitative real-time PCR reagents, optionally along with an instruction manual.

* * * * *

SEQUENCE LISTING

```
<160> NUMBER OF SEQ ID NOS: 58

<210> SEQ ID NO 1
<211> LENGTH: 74
<212> TYPE: DNA
<213> ORGANISM: Cricetulus griseus
<220> FEATURE:
<221> NAME/KEY: gene
<222> LOCATION: (1)..(74)

<400> SEQUENCE: 1
gctggagaga tggctcgagg ttaagagcac tgactgctct tccagaggtc ctgagttcaa      60
ttcccagcaa ccac                                                       74

<210> SEQ ID NO 2
<211> LENGTH: 74
<212> TYPE: DNA
<213> ORGANISM: Cricetulus griseus
<220> FEATURE:
<221> NAME/KEY: gene
<222> LOCATION: (1)..(74)

<400> SEQUENCE: 2
gctggagaga tggctcgagg ttaagagcac tgactgctct tccagaagtc ctgagttcaa      60
ttcccagcaa ccac                                                       74

<210> SEQ ID NO 3
<211> LENGTH: 74
<212> TYPE: DNA
<213> ORGANISM: Cricetulus griseus
<220> FEATURE:
<221> NAME/KEY: gene
<222> LOCATION: (1)..(74)

<400> SEQUENCE: 3
gctggagaga tggctcgagg ttaagagcac tgactgctct tccagaggtc ctgagttcaa      60
ttcccagcaa ccac                                                       74
```

```
<210> SEQ ID NO 4
<211> LENGTH: 74
<212> TYPE: DNA
<213> ORGANISM: Cricetulus griseus
<220> FEATURE:
<221> NAME/KEY: gene
<222> LOCATION: (1)..(74)

<400> SEQUENCE: 4
gctggagaga tggctcgagg ttaagagcac cgactgctct tccagaggtc ctgagttcaa    60
ttcccagcaa ccac                                                     74

<210> SEQ ID NO 5
<211> LENGTH: 74
<212> TYPE: DNA
<213> ORGANISM: Cricetulus griseus
<220> FEATURE:
<221> NAME/KEY: gene
<222> LOCATION: (1)..(74)

<400> SEQUENCE: 5
gctggagaga tggctcgagg ttaagagcac tgactgctct tccagaggtc ctgagttcaa    60
ttcccagcaa ccac                                                     74

<210> SEQ ID NO 6
<211> LENGTH: 74
<212> TYPE: DNA
<213> ORGANISM: Cricetulus griseus
<220> FEATURE:
<221> NAME/KEY: gene
<222> LOCATION: (1)..(74)

<400> SEQUENCE: 6
gctggagaga tggctcgagg ttgagaacac tggctgctct tccagaggtc ctgagttcaa    60
ttcccagcaa ccac                                                     74

<210> SEQ ID NO 7
<211> LENGTH: 20
<212> TYPE: DNA
<213> ORGANISM: Artificial Sequence
<220> FEATURE:
<223> OTHER INFORMATION: A synthetic 5'-3' Forward qPCR primer
<220> FEATURE:
<221> NAME/KEY: prim_transcript
<222> LOCATION: (1)..(20)

<400> SEQUENCE: 7
tggagagatg gctcgaggtt                                               20

<210> SEQ ID NO 8
<211> LENGTH: 21
<212> TYPE: DNA
<213> ORGANISM: Artificial Sequence
<220> FEATURE:
<223> OTHER INFORMATION: A synthetic 5'-3' Reverse qPCR primer
<220> FEATURE:
<221> NAME/KEY: prim_transcript
<222> LOCATION: (1)..(21)

<400> SEQUENCE: 8
tggttgctgg gaattgaact c                                             21

<210> SEQ ID NO 9
<211> LENGTH: 71
<212> TYPE: DNA
<213> ORGANISM: Cricetulus griseus
```

```
<220> FEATURE:
<221> NAME/KEY: gene
<222> LOCATION: (1)..(71)
<223> OTHER INFORMATION: Alu equivalent consensus sequence

<400> SEQUENCE: 9
tggagagatg gctcgaggtt aagagcactg gctgctcttc cagaggtcct gagttcaatt      60
cccagcaacc a                                                          71

<210> SEQ ID NO 10
<211> LENGTH: 22
<212> TYPE: DNA
<213> ORGANISM: Artificial Sequence
<220> FEATURE:
<223> OTHER INFORMATION: A synthetic 5'FAM-3'BHQ qPCR Probe
<220> FEATURE:
<221> NAME/KEY: misc_binding
<222> LOCATION: (1)..(22)
<223> OTHER INFORMATION: 6-carboxyfluorescein (FAM) at the 5' end and
      1-Black hole quencher at the 3' end

<400> SEQUENCE: 10
tggcttgctc ttccagaggt cc                                              22

<210> SEQ ID NO 11
<211> LENGTH: 19
<212> TYPE: DNA
<213> ORGANISM: Artificial Sequence
<220> FEATURE:
<223> OTHER INFORMATION: A synthetic 5'-3' Forward qPCR primer
<220> FEATURE:
<221> NAME/KEY: prim_transcript
<222> LOCATION: (1)..(19)

<400> SEQUENCE: 11
gagatggctc gaggttaag                                                  19

<210> SEQ ID NO 12
<211> LENGTH: 18
<212> TYPE: DNA
<213> ORGANISM: Artificial Sequence
<220> FEATURE:
<223> OTHER INFORMATION: A synthetic 5'-3' Reverse qPCR primer
<220> FEATURE:
<221> NAME/KEY: prim_transcript
<222> LOCATION: (1)..(18)

<400> SEQUENCE: 12
tggttgctgg gaattgaa                                                   18

<210> SEQ ID NO 13
<211> LENGTH: 18
<212> TYPE: DNA
<213> ORGANISM: Artificial Sequence
<220> FEATURE:
<223> OTHER INFORMATION: A synthetic 5'FAM-3'BHQ qPCR Probe
<220> FEATURE:
<221> NAME/KEY: misc_binding
<222> LOCATION: (1)..(18)
<223> OTHER INFORMATION: 6-carboxyfluorescein (FAM) at the 5' end and
      1-Black hole quencher at the 3' end

<400> SEQUENCE: 13
actggctgct tgctcttc                                                   18

<210> SEQ ID NO 14
<211> LENGTH: 19
<212> TYPE: DNA
```

```
<213> ORGANISM: Artificial Sequence
<220> FEATURE:
<223> OTHER INFORMATION: A synthetic 5'-3' Forward qPCR primer
<220> FEATURE:
<221> NAME/KEY: prim_transcript
<222> LOCATION: (1)..(19)

<400> SEQUENCE: 14
tctctaccga gctccaatt                                                19

<210> SEQ ID NO 15
<211> LENGTH: 19
<212> TYPE: DNA
<213> ORGANISM: Artificial Sequence
<220> FEATURE:
<223> OTHER INFORMATION: A synthetic 5'-3' Reverse qPCR primer
<220> FEATURE:
<221> NAME/KEY: prim_transcript
<222> LOCATION: (1)..(19)

<400> SEQUENCE: 15
accaacgacc cttaacttg                                                19

<210> SEQ ID NO 16
<211> LENGTH: 15
<212> TYPE: DNA
<213> ORGANISM: Artificial Sequence
<220> FEATURE:
<223> OTHER INFORMATION: A synthetic 5'FAM-3'BHQ qPCR Probe
<220> FEATURE:
<221> NAME/KEY: misc_binding
<222> LOCATION: (1)..(15)
<223> OTHER INFORMATION: 6-carboxyfluorescein (FAM) at the 5' end and
      1-Black hole quencher at the 3' end

<400> SEQUENCE: 16
cttctcgtcg gtcac                                                    15

<210> SEQ ID NO 17
<211> LENGTH: 22
<212> TYPE: DNA
<213> ORGANISM: Artificial Sequence
<220> FEATURE:
<223> OTHER INFORMATION: A synthetic 5'-3' Reverse qPCR primer
<220> FEATURE:
<221> NAME/KEY: prim_transcript
<222> LOCATION: (1)..(22)

<400> SEQUENCE: 17
ctgcatgtat ccctgcaggc ca                                            22

<210> SEQ ID NO 18
<211> LENGTH: 27
<212> TYPE: DNA
<213> ORGANISM: Artificial Sequence
<220> FEATURE:
<223> OTHER INFORMATION: A synthetic 5'-3' Reverse qPCR primer
<220> FEATURE:
<221> NAME/KEY: prim_transcript
<222> LOCATION: (1)..(27)

<400> SEQUENCE: 18
ggcacatact ttgaagggtt taaaggc                                       27

<210> SEQ ID NO 19
<211> LENGTH: 21
<212> TYPE: DNA
<213> ORGANISM: Artificial Sequence
<220> FEATURE:
```

```
<223> OTHER INFORMATION: A synthetic 5'-3' Forward qPCR primer
<220> FEATURE:
<221> NAME/KEY: prim_transcript
<222> LOCATION: (1)..(21)

<400> SEQUENCE: 19
gctggagaga tggctcgagg t                                              21

<210> SEQ ID NO 20
<211> LENGTH: 24
<212> TYPE: DNA
<213> ORGANISM: Artificial Sequence
<220> FEATURE:
<223> OTHER INFORMATION: A synthetic 5'-3' Reverse qPCR primer
<220> FEATURE:
<221> NAME/KEY: prim_transcript
<222> LOCATION: (1)..(24)

<400> SEQUENCE: 20
accatgtggt tgctgggaat tgaa                                           24

<210> SEQ ID NO 21
<211> LENGTH: 20
<212> TYPE: DNA
<213> ORGANISM: Artificial Sequence
<220> FEATURE:
<223> OTHER INFORMATION: A synthetic 5'FAM-3'BHQ Degenerate qPCR Probe
<220> FEATURE:
<221> NAME/KEY: misc_binding
<222> LOCATION: (1)..(20)
<223> OTHER INFORMATION: 6-carboxyfluorescein (FAM) at the 5' end and
      1-Black hole quencher at the 3' end

<400> SEQUENCE: 21
arcacygrct gctcttccag                                                20

<210> SEQ ID NO 22
<211> LENGTH: 23
<212> TYPE: DNA
<213> ORGANISM: Artificial Sequence
<220> FEATURE:
<223> OTHER INFORMATION: A synthetic 5'-3' Forward qPCR primer
<220> FEATURE:
<221> NAME/KEY: prim_transcript
<222> LOCATION: (1)..(23)

<400> SEQUENCE: 22
gctggagaga tggctcgagg tta                                            23

<210> SEQ ID NO 23
<211> LENGTH: 22
<212> TYPE: DNA
<213> ORGANISM: Artificial Sequence
<220> FEATURE:
<223> OTHER INFORMATION: A synthetic 5'-3' Reverse qPCR primer
<220> FEATURE:
<221> NAME/KEY: prim_transcript
<222> LOCATION: (1)..(22)

<400> SEQUENCE: 23
gtggttgctg ggaattgaac tc                                             22

<210> SEQ ID NO 24
<211> LENGTH: 21
<212> TYPE: DNA
<213> ORGANISM: Artificial Sequence
<220> FEATURE:
<223> OTHER INFORMATION: A synthetic 5'FAM-3'BHQ Degenerate qPCR Probe
<220> FEATURE:
```

```
<221> NAME/KEY: misc_binding
<222> LOCATION: (1)..(21)
<223> OTHER INFORMATION: 6-carboxyfluorescein (FAM) at the 5' end and
      1-Black hole quencher at the 3' end

<400> SEQUENCE: 24
ctgctcttcc agargtcctg a                                                 21

<210> SEQ ID NO 25
<211> LENGTH: 22
<212> TYPE: DNA
<213> ORGANISM: Artificial Sequence
<220> FEATURE:
<223> OTHER INFORMATION: A synthetic 5'-3' Forward primer
<220> FEATURE:
<221> NAME/KEY: prim_transcript
<222> LOCATION: (1)..(22)

<400> SEQUENCE: 25
ttggtggcac acacctttaa tc                                                22

<210> SEQ ID NO 26
<211> LENGTH: 23
<212> TYPE: DNA
<213> ORGANISM: Artificial Sequence
<220> FEATURE:
<223> OTHER INFORMATION: A synthetic 5'-3' Reverse primer US12/476101
<220> FEATURE:
<221> NAME/KEY: prim_transcript
<222> LOCATION: (1)..(23)

<400> SEQUENCE: 26
gctggctctt gaactcacag aga                                               23

<210> SEQ ID NO 27
<211> LENGTH: 80
<212> TYPE: DNA
<213> ORGANISM: Artificial Sequence
<220> FEATURE:
<223> OTHER INFORMATION: A synthetic Alu sequence US12/476101.
<220> FEATURE:
<221> NAME/KEY: gene
<222> LOCATION: (1)..(80)

<400> SEQUENCE: 27
cattggtggc acaccctttt aatcccagca ctcgggaggc agaggcaggt ggatctctgt       60
gagttcaaga gccagcctgg                                                   80

<210> SEQ ID NO 28
<211> LENGTH: 134
<212> TYPE: DNA
<213> ORGANISM: Artificial Sequence
<220> FEATURE:
<223> OTHER INFORMATION: A synthetic Alu sequence US990300
<220> FEATURE:
<221> NAME/KEY: gene
<222> LOCATION: (1)..(134)

<400> SEQUENCE: 28
ccaggcattg gtggcacaca cctttagtcc cagcactcag gaggcagagg caggaggatc       60
acttgagttc aagagccagc ctggtctacc agagttcctg agttcaagcc aggctataca      120
gagaaaccct gtct                                                        134

<210> SEQ ID NO 29
<211> LENGTH: 17
<212> TYPE: DNA
```

```
<213> ORGANISM: Artificial Sequence
<220> FEATURE:
<223> OTHER INFORMATION: A synthetic 5'-3' Forward primer US990300
<220> FEATURE:
<221> NAME/KEY: prim_transcript
<222> LOCATION: (1)..(17)

<400> SEQUENCE: 29
ccaggcattg gtggcac                                                        17

<210> SEQ ID NO 30
<211> LENGTH: 17
<212> TYPE: DNA
<213> ORGANISM: Artificial Sequence
<220> FEATURE:
<223> OTHER INFORMATION: A synthetic 5'-3' Reverse primer US990300
<220> FEATURE:
<221> NAME/KEY: prim_transcript
<222> LOCATION: (1)..(17)

<400> SEQUENCE: 30
agacagggtt tctctgt                                                        17

<210> SEQ ID NO 31
<211> LENGTH: 71
<212> TYPE: DNA
<213> ORGANISM: Cricetulus griseus
<220> FEATURE:
<221> NAME/KEY: gene
<222> LOCATION: (1)..(71)
<223> OTHER INFORMATION: Complementary to SEQ ID NO: 9

<400> SEQUENCE: 31
acctctctac cgagctccaa ttctcgtgac cgacgagaag gtctccagga ctcaagttaa         60
gggtcgttgg t                                                              71

<210> SEQ ID NO 32
<211> LENGTH: 254
<212> TYPE: DNA
<213> ORGANISM: Artificial Sequence
<220> FEATURE:
<223> OTHER INFORMATION: A synthetic sequence; sequence 21 in alignment
      for primer design

<400> SEQUENCE: 32
tggagagatg gctcgaggtt aagagcactg gctgttcttc cagaggtcct gagttcaatt         60
ctcagcaacc acatgatgac tcaaaatcat ctataatgag atctggtgcc ccctttggt         120 gggaaggcat acatgcaagc gaagactaca taatcaatct ttttttttt ttttggcct         180 gtggggacat tttgttcaaa ccatcccagt gtgtgtgtgt gtgtgtgtgt gtgtgagaga        240
gagagagaga gaga                                                          254

<210> SEQ ID NO 33
<211> LENGTH: 252
<212> TYPE: DNA
<213> ORGANISM: Artificial Sequence
<220> FEATURE:
<223> OTHER INFORMATION: A synthetic sequence; sequence 50 in alignment
      for primer design

<400> SEQUENCE: 33
tggagagatg gctcgaggta agagcactgg ctgttcttca gaggtcctga gttcattctc         60
agcaaccaca tgatgactca aaatcatcta taatgagatc tggtgccccc ttttggtggg       120
aaggcataca tgcaagcgaa gactacataa tcaatctttt tttttttttt tttggcctgt       180
```

```
ggggacattt tgttcaaacc atcccagtgt gtgtgtgtgt gtgtgtgtgt gtgagagaga      240
gagagagaga ga                                                         252
```

<210> SEQ ID NO 34
<211> LENGTH: 254
<212> TYPE: DNA
<213> ORGANISM: Artificial Sequence
<220> FEATURE:
<223> OTHER INFORMATION: A synthetic sequence; sequence 7R in alignment
      for primer design

<400> SEQUENCE: 34

```
cgatatggag agatggctcg aggttaagag cactggctgt tcttccagag gtcctgagtt      60
caattctcag caaccacatg atgactcaaa atcatctata atgagatctg gtgccccctt     120
ttggtgggaa ggcatacatg caagcgaaga ctacataatc aatctttttt tttttttttt     180
ggcctgtggg gacattttgt tcaaaccatc ccagtgtgtg tgtgtgtgtg tgtgtgtgtg     240
agagagagag agag                                                      254
```

<210> SEQ ID NO 35
<211> LENGTH: 292
<212> TYPE: DNA
<213> ORGANISM: Artificial Sequence
<220> FEATURE:
<223> OTHER INFORMATION: A synthetic sequence; sequence 11 in alignment
      for primer design

<400> SEQUENCE: 35

```
ttgcatgcag gcctctgcag tcgacgggcc cgggatccga tttggagaga tggctcgagg      60
ttagagcact ggctgttctt ccagaggtcc tgagttcaat tctcagcaac cacatgatga    120
ctcaaaatca tctataatga gatctggtgc cccttttgg tgggaaggca tacatgcaag     180
cgaagactac ataatcaatc tttttttttt tttggcctgt ggggacattt tgttcaaacc    240
atcccagtgt gtgtgtgtgt gtgtgtgtgt gtgagagaga gagagagaga ga            292
```

<210> SEQ ID NO 36
<211> LENGTH: 292
<212> TYPE: DNA
<213> ORGANISM: Artificial Sequence
<220> FEATURE:
<223> OTHER INFORMATION: A synthetic sequence; sequence 27R in alignment
      for primer design

<400> SEQUENCE: 36

```
ttgcatgcag gcctctgcag tcgacgggcc cgggatccga tttggagaga tggctcgagg      60
ttagagcact ggctgctctt ccagaggtct tgaattcaat ttccagcaac aacatggtgg    120
ctcacaacca tacatgatga gatctggtgc cctctcctgg cctgcaggga tacatgcaga    180
cagaatacta tatacataat acaaacaaat aaataaataa gtaaatatta ttaaaggtgt    240
gtgtcaccat gtctggcaat aatcatgtcc ttttgtaata tttactttgt gt            292
```

<210> SEQ ID NO 37
<211> LENGTH: 292
<212> TYPE: DNA
<213> ORGANISM: Artificial Sequence
<220> FEATURE:
<223> OTHER INFORMATION: A synthetic sequence; sequence 13 in alignment
      for primer design

<400> SEQUENCE: 37

```
ttgcatgcag gcctctgcag tcgacgggcc cgggatccga tttggagaga tggctcgagg      60
ttaagagcac tggctgctct tccagaggtc ttgaattcaa tttccagcaa caacatggtg     120
gctcacaacc atacatgatg agatctggtg ccctctctgg cctgcaggga tacatgcaga     180
cagaatacta tatacataat acaaacaaat aaataaataa gtaaatatta ttaaaggtgt     240
gtgtcaccat gtctggcaat aatcatgtcc ttttgtaata tttactttgt gt             292
```

<210> SEQ ID NO 38
<211> LENGTH: 356
<212> TYPE: DNA
<213> ORGANISM: Artificial Sequence
<220> FEATURE:
<223> OTHER INFORMATION: A synthetic sequence; sequence 8 in alignment
      for primer design

<400> SEQUENCE: 38

```
tggagagatg gctcgaggtt aagagcactg gctgctcttc tagaggacag gattcaaatc      60
ccagcactca catggtaggt cacaactctc tgtaacccag gggatccaac accctcacat     120
agacattcat gcaggcaaaa cattgcacat aaaattaagt ttaaaaacaa acaggaatc     180 ccagactgaa tctttaaaaa agaaagaaaa gaaaagaaa atgccttcca gttggttaag     240
gttggttaca gtgcccttgt atctctgtat tgtaatagcc tttaaaccct tcaaagtatg     300
tgccatttta aaattctaaa atcaaaggcc agagagagag agagagagag agagag         356
```

<210> SEQ ID NO 39
<211> LENGTH: 369
<212> TYPE: DNA
<213> ORGANISM: Artificial Sequence
<220> FEATURE:
<223> OTHER INFORMATION: A synthetic sequence; sequence 42 in alignment
      for primer design

<400> SEQUENCE: 39

```
ttggagagat ggctcgaggt taagagcact ggctgctctt ctagaggaag gattcaaatc      60
ccagcactca catggtaggt cacaactctc tgtaacccag gggatccaac accctcacat     120
agacattcat gcaggcaaaa cattgcacat aaaattaagt ttaaaaacaa acaggaatc     180 ccagactgaa tctttaaaaa agaaagaaaa gaaaagaaa atgccttcca gttggttaag     240
gttggttaca gtgcccttgt atctctgtat tgtaatagcc tttaaaccct tcaaagtatg     300
tgccatttta aaattctaaa atcaaaggcc agagagagag agagagagag agagagagag     360
agagagaga                                                            369
```

<210> SEQ ID NO 40
<211> LENGTH: 368
<212> TYPE: DNA
<213> ORGANISM: Artificial Sequence
<220> FEATURE:
<223> OTHER INFORMATION: A synthetic sequence; sequence 37 in alignment
      for primer design

<400> SEQUENCE: 40

```
ttggagagat ggctcgaggt taagagcact ggctgctctt ctagaggaag gattcaatcc      60
cagcactcac atggtaggtc acaactctct gtaacccagg ggatccaaca ccctcacata     120
gacattcatg caggcaaaac attgcacata aaattaagtt taaaacaaa acaggaatcc     180 cagactgaat ctttaaaaaa gaaagaaaag aaaagaaaa tgccttccag ttggttaagg     240
ttggttacag tgcccttgta tctctgtatt gtaatagcct ttaaacccct tcaaagtatgt    300
```

```
gccatttttaa aattctaaaa tcaaaggcca gagagagaga gagagagaga gagagagaga    360
gagagaga                                                              368
```

<210> SEQ ID NO 41
<211> LENGTH: 366
<212> TYPE: DNA
<213> ORGANISM: Artificial Sequence
<220> FEATURE:
<223> OTHER INFORMATION: A synthetic sequence; sequence 26 in alignment
      for primer design

<400> SEQUENCE: 41

```
tttggagaga tggctcgagg ttagagcact ggctgctctt ctagaggaag gattcaatcc     60
cagcactcac atggtaggtc acaactctct gtaacccagg ggatccaaca ccctcacata    120
gacattcatg caggcaaaac attgcacata aaattaagtt taaaaacaaa acaggaatcc    180
cagactgaat ctttaaaaaa gaaagaaaag aaaagaaaa tgccttccag ttggttaagg     240
ttggttacag tgcccttgta tctctgtatt gtaatagcct ttaaaccctt caaagtatgt    300 gccatttttaa aattctaaaa tcaaaggcca gagagagaga gagagagaga gagagagaga   360
gagaga                                                               366
```

<210> SEQ ID NO 42
<211> LENGTH: 420
<212> TYPE: DNA
<213> ORGANISM: Artificial Sequence
<220> FEATURE:
<223> OTHER INFORMATION: A synthetic sequence; sequence 22 in alignment
      for primer design

<400> SEQUENCE: 42

```
agggaaagct tgcatgcagg cctctgcagt cgacgggccc gggatccgat ttggagagat     60
ggctcgaggt taagagcact ggctgctctt ctagaggaca ggattcaaat cccagcactc    120
acatggtagg tcacaactct ctgtaaccca ggggatccaa caccctcaca tagacattca    180
tgcaggcaaa acattgcaca taaaattaag tttaaaaaca aaacaggaat cccagactga    240
atctttaaaa aagaaagaaa agaaaaagaa aatgccttcc agttggttaa ggttggttac    300
agtgcccttg tatctctgta ttgtaatagc ctttaaaccc ttcaaagtat gtgccatttt    360
aaaattctaa aatcaaaggc cagagagaga gagagagaga gagagagaga gagagagaga    420
```

<210> SEQ ID NO 43
<211> LENGTH: 79
<212> TYPE: DNA
<213> ORGANISM: Cricetulus griseus
<220> FEATURE:
<223> OTHER INFORMATION: comprises SEQ ID NO: 9

<400> SEQUENCE: 43

```
gctggagaga tggctcgagg ttaagagcac tggctgctct tccagaggtc ctgagttcaa     60
ttcccagcaa ccacatggt                                                  79
```

<210> SEQ ID NO 44
<211> LENGTH: 79
<212> TYPE: DNA
<213> ORGANISM: Cricetulus griseus
<220> FEATURE:
<221> NAME/KEY: gene
<223> OTHER INFORMATION: Complementary to SEQ ID NO: 43

<400> SEQUENCE: 44
cgacctctct accgagctcc aattctcgtg accgacgaga aggtctccag gactcaagtt    60
aagggtcgtt ggtgtacca                                                 79

<210> SEQ ID NO 45
<211> LENGTH: 74
<212> TYPE: DNA
<213> ORGANISM: Cricetulus griseus
<220> FEATURE:
<221> NAME/KEY: gene
<222> LOCATION: complementary to SEQ ID NO: 1

<400> SEQUENCE: 45
cgacctctct accgagctcc aattctcgtg accgacgaga aggtctccag gactcaagtt    60
aagggtcgtt ggtc                                                      74

<210> SEQ ID NO 46
<211> LENGTH: 73
<212> TYPE: DNA
<213> ORGANISM: Artificial Sequence
<220> FEATURE:
<223> OTHER INFORMATION: A synthetic sequence; sequence 200BP in
      alignment of residual CHO DNA

<400> SEQUENCE: 46
gctggagaga tggctcgagg ttaagagcac cgactgctct tccagaggtc ctgagttcaa    60
ttcccagcaa cca                                                       73

<210> SEQ ID NO 47
<211> LENGTH: 73
<212> TYPE: DNA
<213> ORGANISM: Artificial Sequence
<220> FEATURE:
<223> OTHER INFORMATION: A synthetic sequence; sequence US6 in alignment
      of residual CHO DNA

<400> SEQUENCE: 47
gctggagaga tggctcgagg ttaagagcac tgactgctct tccagaggtc ctgagttcaa    60
ttcccagcaa cca                                                       73

<210> SEQ ID NO 48
<211> LENGTH: 73
<212> TYPE: DNA
<213> ORGANISM: Artificial Sequence
<220> FEATURE:
<223> OTHER INFORMATION: A synthetic sequence; sequence 2FG in alignment
      of residual CHO DNA

<400> SEQUENCE: 48
gctggagaga tggctcgagg ttaagagcac tgactgctct tccagaagtc ctgagttcaa    60
ttcccagcaa cca                                                       73

<210> SEQ ID NO 49
<211> LENGTH: 73
<212> TYPE: DNA
<213> ORGANISM: Artificial Sequence
<220> FEATURE:
<223> OTHER INFORMATION: A synthetic sequence; sequence 49 in alignment
      of residual CHO DNA

<400> SEQUENCE: 49
gctggagaga tggctcgagg ttaagagcac tggctgctct tccagaggtc ctgagttcaa    60
ttcccagcaa cca                                                       73

<210> SEQ ID NO 50
<211> LENGTH: 73
<212> TYPE: DNA
<213> ORGANIZM: Artificial Sequence
<220> FEATURE:
<223> OTHER INFORMATION: A synthetic sequence; sequence US8 in alignment of residual CHO DNA

<400> SEQUENCE: 50
gctggagaga tggctcgagg ttgagaacac tggctgctct tccagaggtc ctgagttcaa    60
ttcccagcaa cca    73

<210> SEQ ID NO 51
<211> LENGTH: 78
<212> TYPE: DNA
<213> ORGANISM: Artificial Sequence
<220> FEATURE:
<223> OTHER INFORMATION: A synthetic sequence; sequence 5RP1 in alignment of residual CHO DNA

<400> SEQUENCE: 51
gctggagaga tggctcgagg ttaagagcac tggctgctct tctagaggac aggattcaat    60
ttccagcaac aacatggt    78

<210> SEQ ID NO 52
<211> LENGTH: 79
<212> TYPE: DNA
<213> ORGANISM: Artificial Sequence
<220> FEATURE:
<223> OTHER INFORMATION: A synthetic sequence; sequence 6RP2 in alignment of residual CHO DNA

<400> SEQUENCE: 52
gctggagaga tggctcgagg ttaagagcac tggctgctct tccagaggtc ttgaattcaa    60
tttccagcaa caacatggt    79

<210> SEQ ID NO 53
<211> LENGTH: 79
<212> TYPE: DNA
<213> ORGANISM: Cricetulus griseus

<400> SEQUENCE: 53
cattggtggc acactccttt aatcccagca ctcgggaggc agaggcaggc ggatctctgt    60
gagttcgagg ccagcctgg    79

<210> SEQ ID NO 54
<211> LENGTH: 136
<212> TYPE: DNA
<213> ORGANISM: Cricetulus griseus

<400> SEQUENCE: 54
ccaggcattg gtggcacaca cctttagtcc cagcaagtgg aaggcagagg caggcaaatt    60
tgtaagtaca aggccagcct ggtctacaga gtaagtgcca ggatacgctc caaagctaca    120
cagagaaacc ctgtct    136

<210> SEQ ID NO 55
<211> LENGTH: 73
<212> TYPE: DNA
<213> ORGANISM: Mus musculus

<400> SEQUENCE: 55

```
gctggagaga tggctcgagg ttgagaacac tggctgctct tccagaggtc ctgagttcaa    60
ttcccagcaa cca                                                      73

<210> SEQ ID NO 56
<211> LENGTH: 71
<212> TYPE: DNA
<213> ORGANISM: Mus musculus

<400> SEQUENCE: 56
gctggagaga tggctcgagg ttaagagcac cgactgctct ttccgaaggt cctgagttca    60
attcccagca a                                                        71

<210> SEQ ID NO 57
<211> LENGTH: 75
<212> TYPE: DNA
<213> ORGANISM: Mus musculus

<400> SEQUENCE: 57
ctggagagat ggctcgaggt taaaaacact gactgttctc ttccggaagt tctgagttca    60
attcccagca accac                                                    75

<210> SEQ ID NO 58
<211> LENGTH: 75
<212> TYPE: DNA
<213> ORGANISM: Mus musculus

<400> SEQUENCE: 58
ctggagagat ggctcgaggt taaaaacact gactgttctc ttccggaagt tctgagttca    60
attcccagca accac                                                    75
```